(12) United States Patent
Hamamah et al.

(10) Patent No.: US 10,731,218 B2
(45) Date of Patent: *Aug. 4, 2020

(54) METHODS EMPLOYING CIRCULATING DNA AND MIRNA AS BIOMARKERS FOR FEMALE INFERTILITY

(71) Applicants: INSERM (INSTITUT NATIONAL DE LA SANTÉ ET DE LA RECHERCHE MÉDICALE), Paris (FR); UNIVERSITE DE MONTPELLIER, Montpellier (FR); CENTRE HOSPITALIER UNIVERSITAIRE DE MONTPELLIER, Montpellier (FR)

(72) Inventors: Samir Hamamah, Montpellier (FR); Sabine Traver, Montpellier (FR); Elodie Scalici, Montpellier (FR)

(73) Assignees: INSERM (INSTITUT NATIONAL DE LA SANTE ET DE LA RECHERCHE MEDICALE), Paris (FR); UNIVERSITE DE MONTPELLIER, Montpellier (FR); CENTRE HOSPITALIER UNIVERSITAIRE DE MONTPELLIER, Montpellier (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/447,221

(22) Filed: Jun. 20, 2019

(65) Prior Publication Data

US 2019/0367987 A1 Dec. 5, 2019

Related U.S. Application Data

(63) Continuation of application No. 15/321,230, filed as application No. PCT/EP2015/064609 on Jun. 26, 2015, now Pat. No. 10,400,282.

(30) Foreign Application Priority Data

Jun. 27, 2014 (EP) ..................................... 14306042

(51) Int. Cl.
*C12Q 1/6883* (2018.01)
*G16H 10/60* (2018.01)

(52) U.S. Cl.
CPC ........... *C12Q 1/6883* (2013.01); *G16H 10/60* (2018.01); *C12Q 2600/106* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

FOREIGN PATENT DOCUMENTS

WO WO 2014/020564 * 2/2014

OTHER PUBLICATIONS

Ghorai (Frontiers in Genetics Apr. 2014 vol. 5 article 100).*
Noferesti (Journal of Ovarian Research 20515 8:81 pp. 1-16).*
Wang (PloS One Jul. 2012 7(7);e41561).*
Umetani (Ann NY Acad Sci 1075 pp. 299-307 (2006)).*
Hamamah (Abstracts of the 31st Annual Meeting of Eshre Lisbon, Portugal Jun. 14-17, 2015).*

* cited by examiner

*Primary Examiner* — Amanda Haney
(74) *Attorney, Agent, or Firm* — W&C IP

(57) ABSTRACT

The present invention relates generally to the fields of reproductive medicine. More specifically, the present invention relates to methods for determining the ovarian reserve and ovarian function by determining the level of cell-free nucleic acids or the level of a miRNA species selected from miR_30_a or miR_140 or let_7_b or miR_191 or miR_320_a or miR_21 or miR_30_d or miR_574_3p. The method may also be used in predicting the efficacy of controlled ovarian hyperstimulation.

1 Claim, 15 Drawing Sheets

Figure 3:
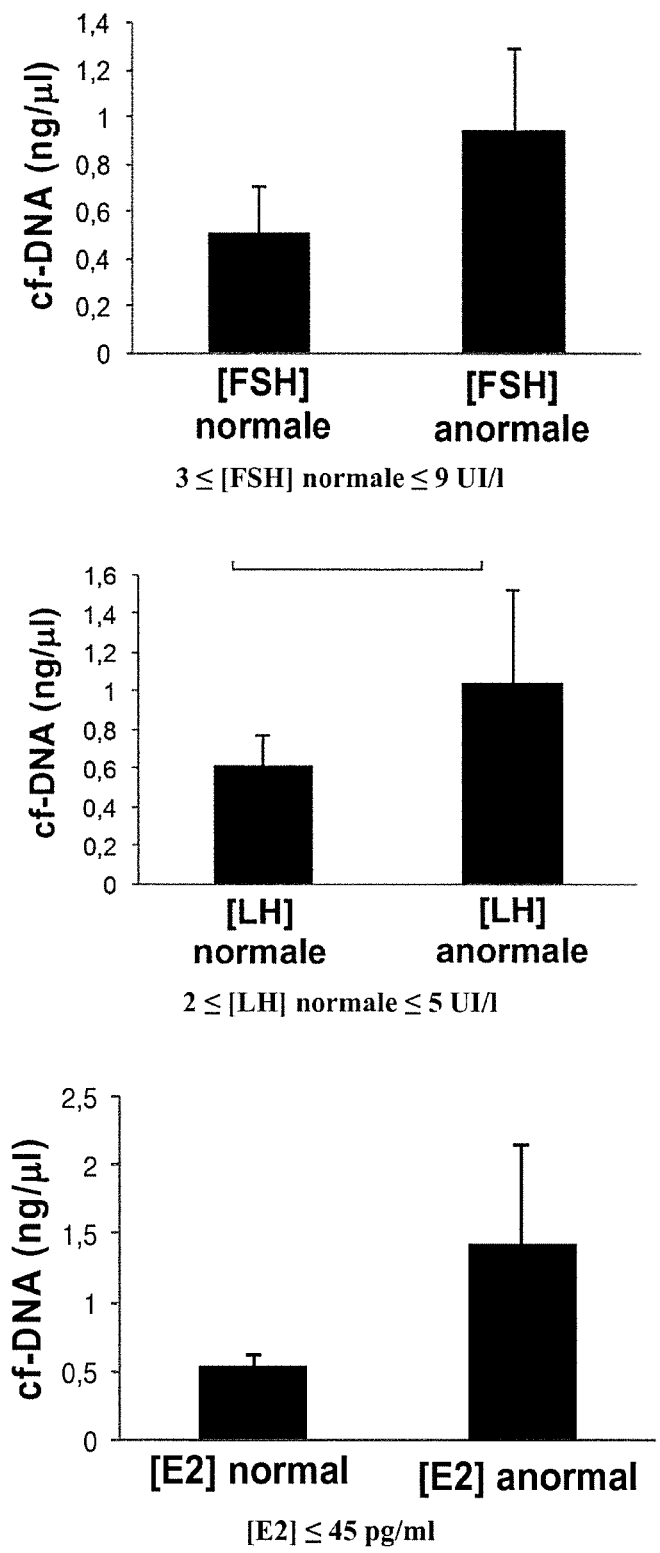

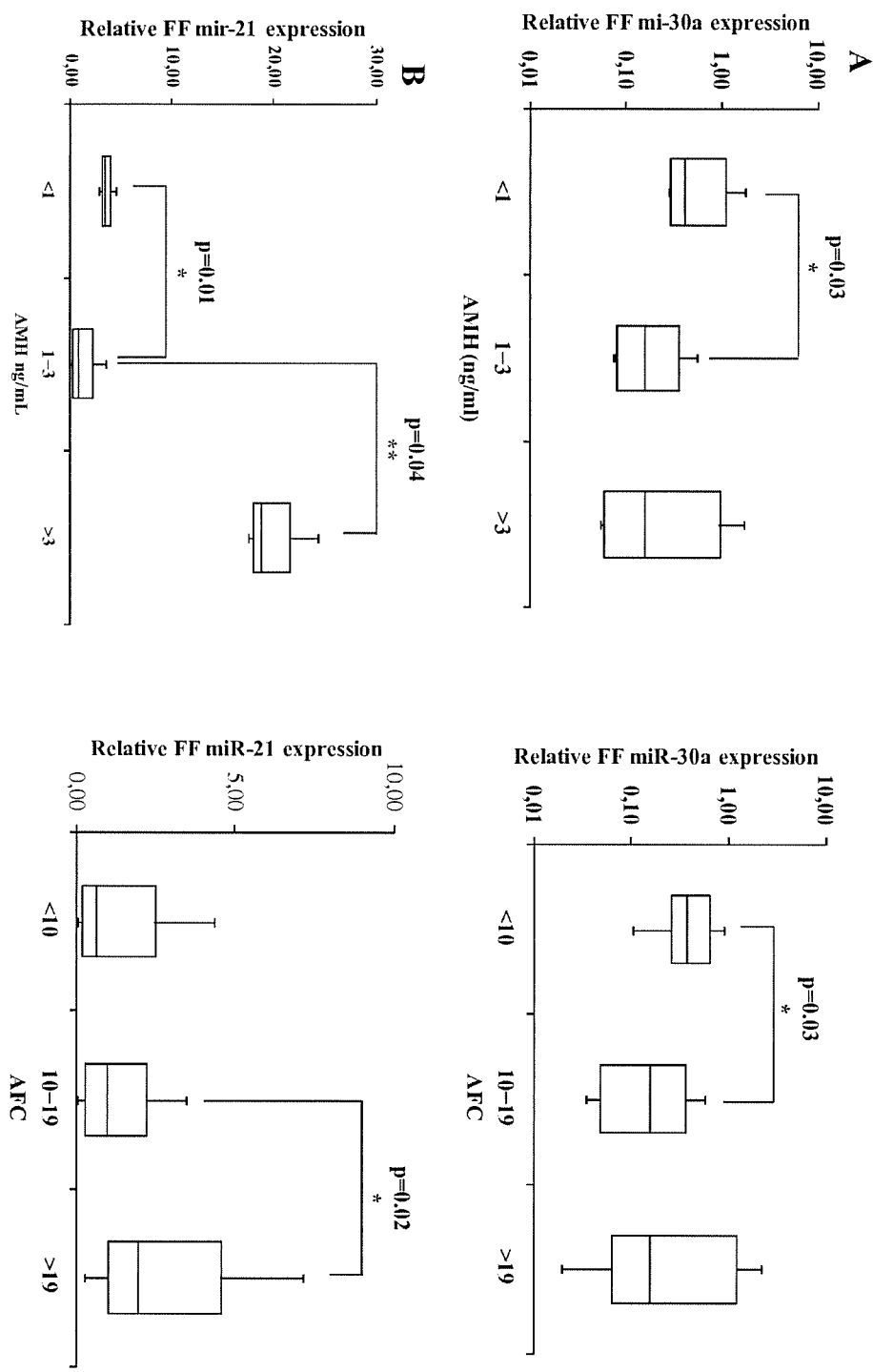
Figure 1 A and B

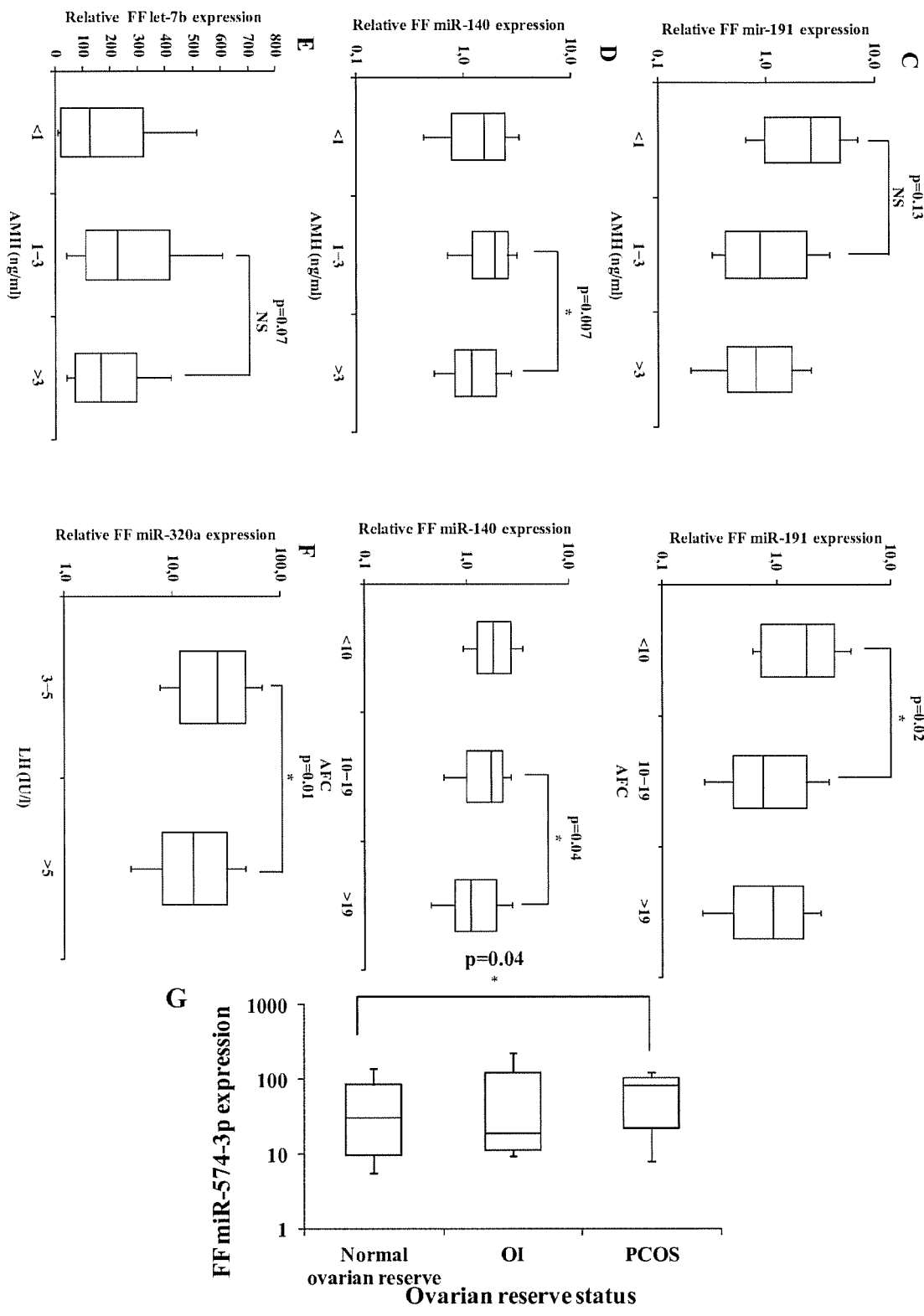
Figure 1 C-G

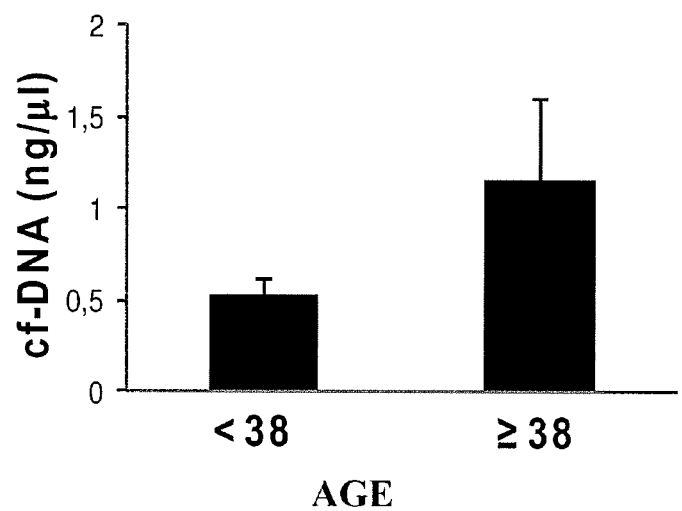
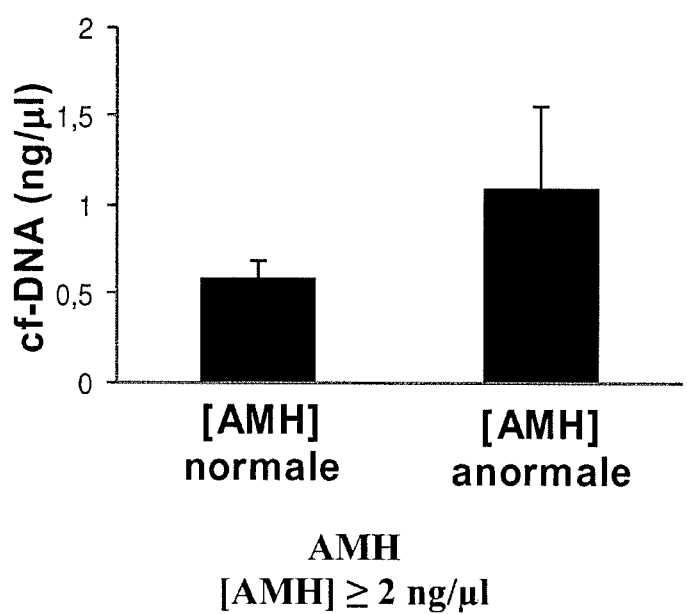
Figure 2

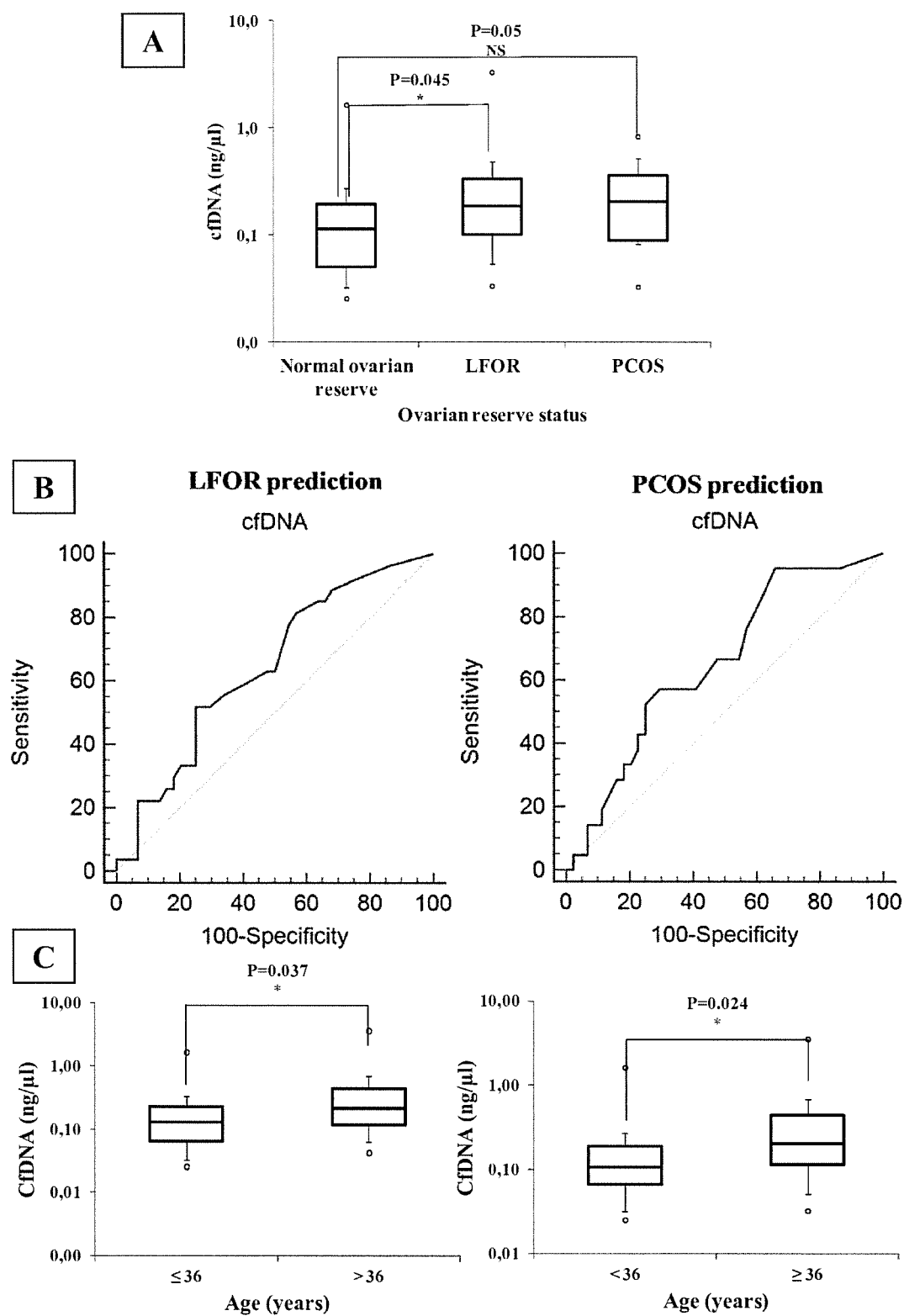
Figure 12A, B and C

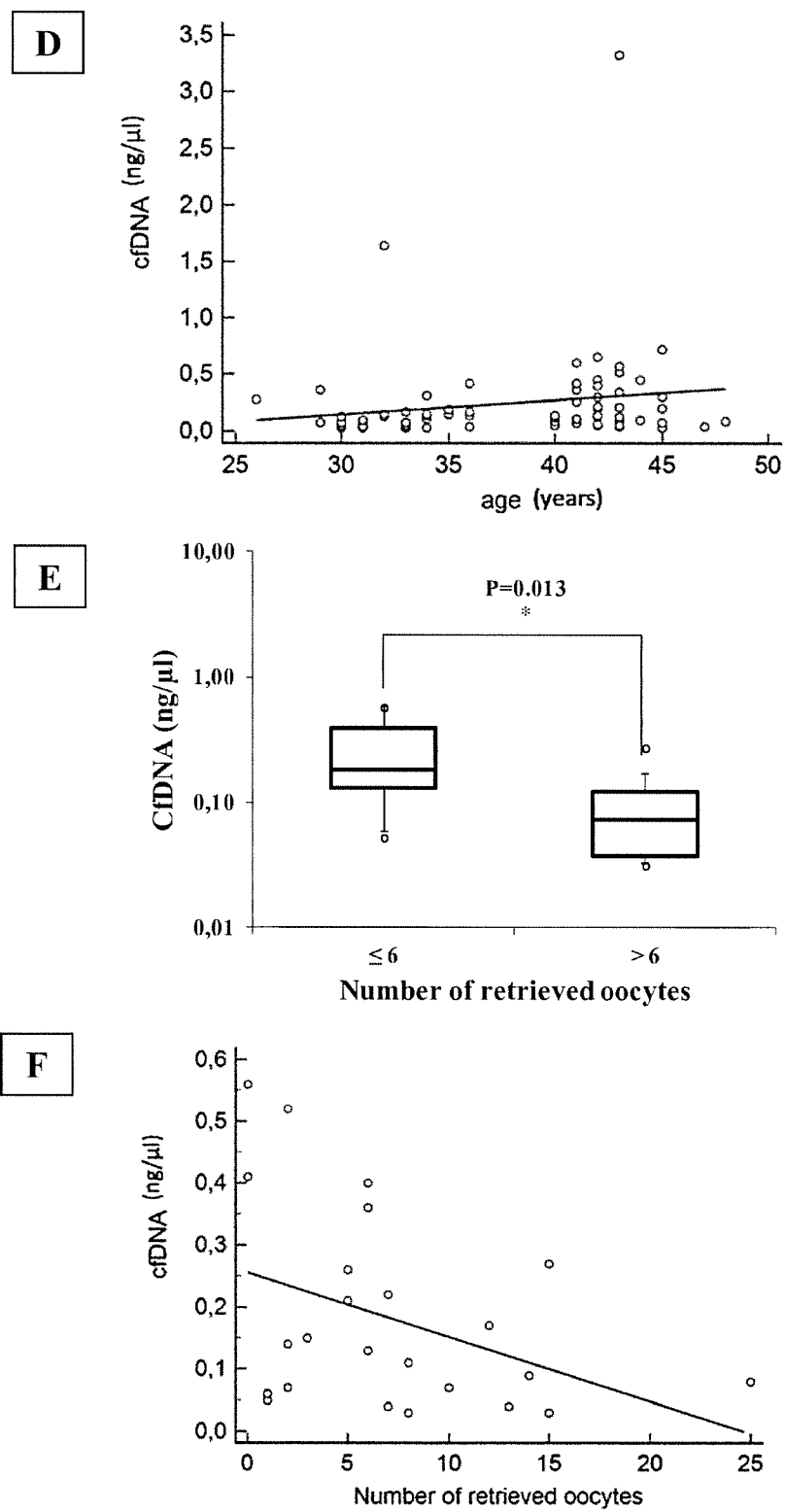
Figure 12 D, E and F

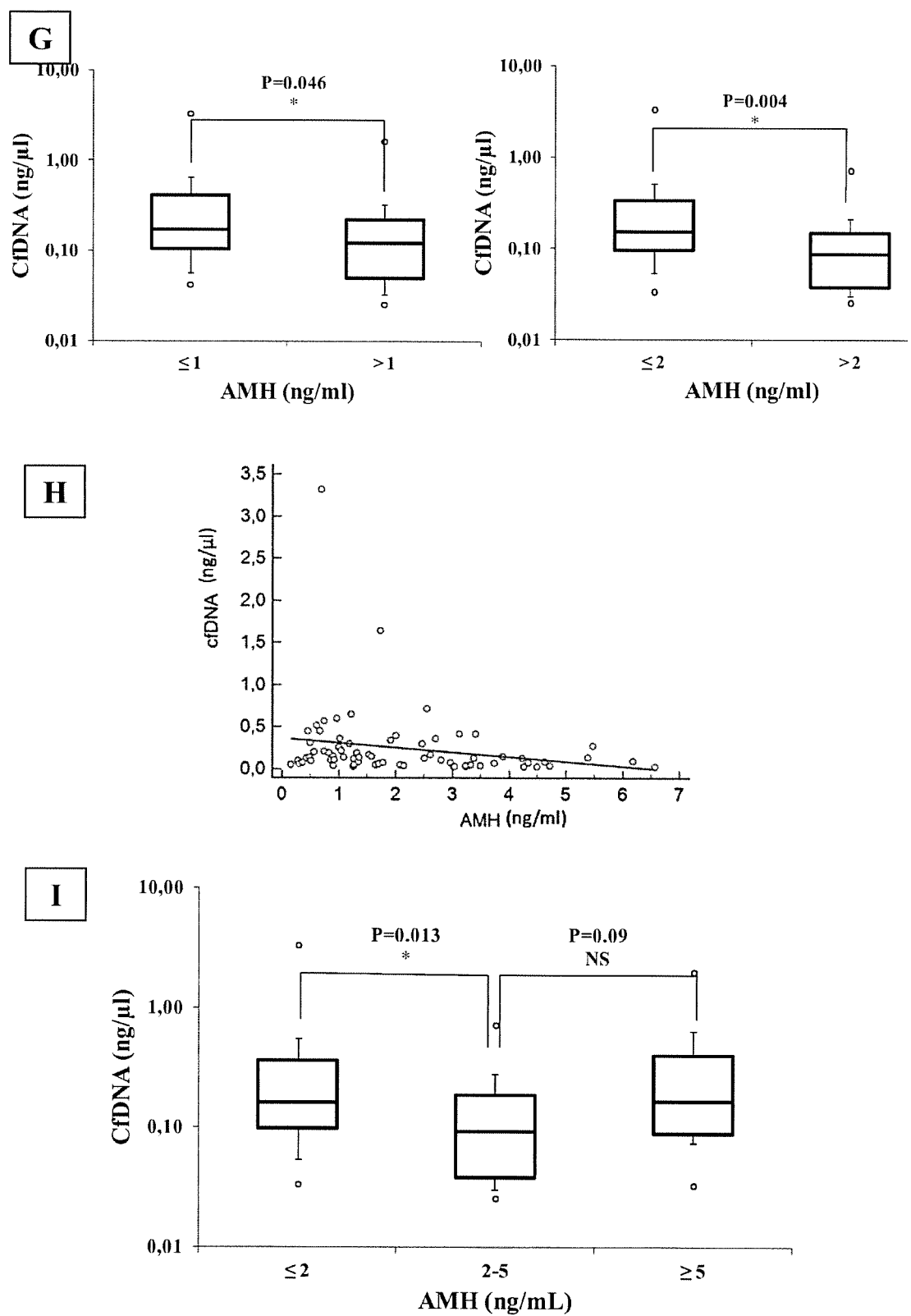
Figure 12 G, H and I

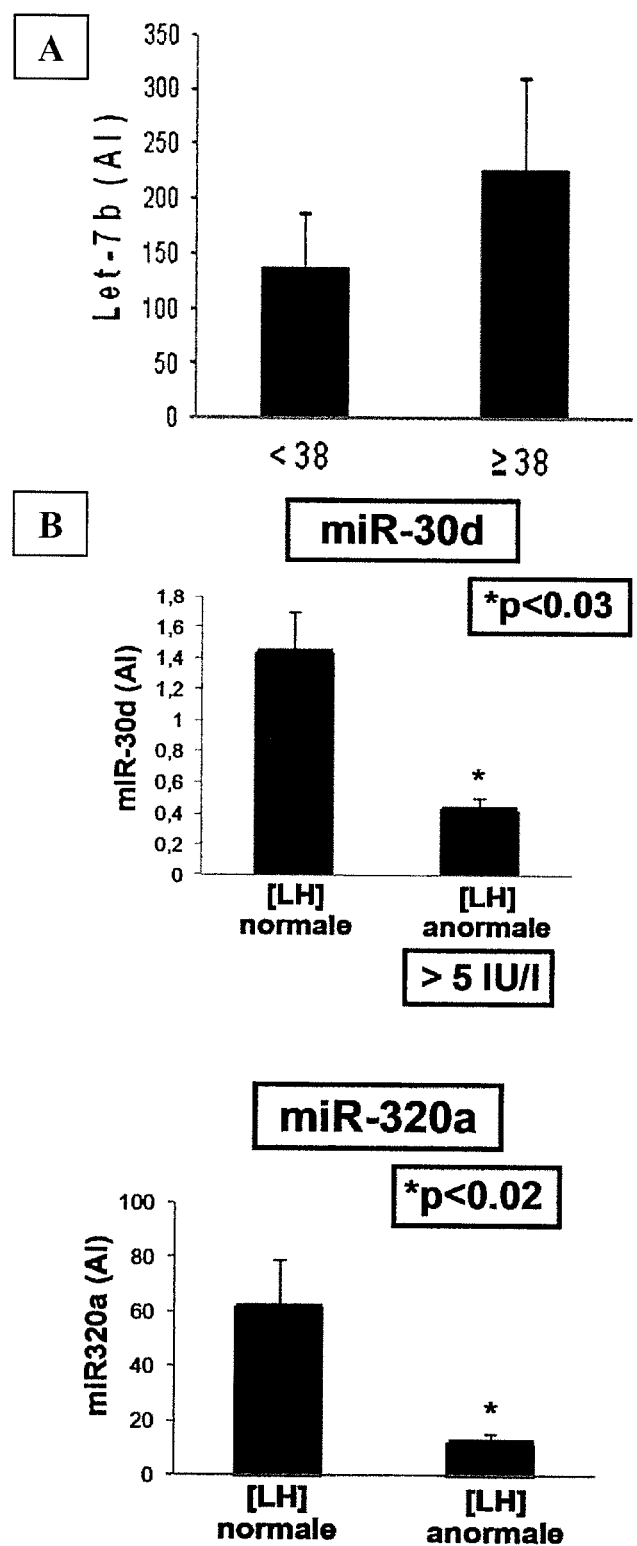
Figure 13 A and B

METHODS EMPLOYING CIRCULATING DNA AND MIRNA AS BIOMARKERS FOR FEMALE INFERTILITY

CROSS-REFERENCE TO RELATED APPLICATIONS

This application is a continuation of U.S. Ser. No. 15/321,230 filed on Dec. 22, 2016, now U.S. Pat. No. 10,400,282, which itself was a Rule 371 filing from PCT/EP2015/064609 filed Jun. 26, 2015, and that international application claimed priority to European Application 14306042.4 filed Jun. 27, 2014.

FIELD OF THE INVENTION

The present invention relates generally to the fields of reproductive medicine. More specifically, the present invention relates to methods and kits for determining the ovarian reserve and ovarian function.

BACKGROUND OF THE INVENTION

Currently, there is no reliable commercially available cell-free nucleic acid quantification approach for estimating woman ovarian reserve, predicting woman stimulation response, IVF outcome and no therapy targeting these cell-free nucleic acids to improve ART success.

In vitro fertilization (IVF) and intracytoplasmic sperm injection (ICSI) data, clearly indicates disappointing results, even in the most successful programs. Indeed, in France, the ART success rate ranges from 25% to 28% in terms of live birth per oocyte retrieval. Some defects leading to problems with embryo implantation are still unexplained and the presence of abnormal levels of cell-free nucleic acids in blood could constitute another area of unexplained infertility.

During follicular development, oocytes are in close contact with the surrounding cumulus cells (CCs) to form the cumulus-oocyte complex (COC). The crosstalk between oocytes and CCs occurs through gap junctions (Albertini et al., 2001). This paracrine signaling is crucial for the acquisition of developmental competence in oocytes and CCs (Gilchrist et al., 2008). These reciprocal regulations are carefully modulated by some key genes that are themselves regulated by miRNAs (Assou et al., 2013). MicroRNAs belong to the "small RNA" family and are evolutionarily conserved from invertebrates to vertebrates (Lagos-Quintana et al., 2001). MiRNAs were first identified in *Caenorhabditis elegans* at the beginning of the nineties (Lee et al., 1993). They are non-coding single-stranded RNA molecules of 19-25 nucleotides in length that arise from intergenic or intragenic genomic regions. In mammals, miRNAs are usually complementary to a small region in the 3' UTR (untranslated region) of messenger RNAs (mRNAs).

Some miRNAs are found in body fluids. As they are contained in exosomes, they are highly stable in body fluids because protected from RNAses. The potential use of these circulating miRNAs as novel, non-invasive diagnostic/prognostic biomarkers is the focus of many investigations (Mitchell et al., 2008) and they are already used as biomarkers for the diagnosis and prognosis of several gynecological and pregnancy disorders (Carletti et al., 2009). MicroRNAs (miRNAs) are small (19-25 nucleotides), single-stranded, non-coding RNA molecules that bind specifically to and post-transcriptionnally regulate several messenger RNAs (mRNAs) (Thomas et al., 2010). MiRNAs play important physiological roles and miRNA dysregulations can lead to pathologies. In fertility, miRNAs are associated with the functional regulation of gonadal somatic cells (Leydig and Sertoli cells in testis, and granulosa and cumulus cells in the ovary) involved in steroid synthesis. For example, in male mice, deletion of Dicer (a protein essential for miRNA maturation) in Sertoli cells leads to infertility due to the complete absence of spermatozoa and progressive testicular degeneration (Hossain et al., 2012). In female mice, Dicer invalidation leads to infertility due to multiple defects in ovarian functions, including abnormal cycles and abnormal response to gonadotropin leading to ovulation problem (Nagaraja et al., 2008). MiRNAs could have a major role in the regulation of follicular cell functions, such as steroidogenesis, apoptosis, luteinization, as well as in ovulation process (Hawkins et al., 2010). For instance, treatment of mouse mural granulosa cells with luteinizing hormone leads to the deregulation of a set of miRNAs (particularly miR-132 and miR-212 overexpression) that are possibly important for the control of ovarian functions (Fiedler et al., 2008). Overexpression of miR-93 could disturb ovary development. Indeed, miR-93 targets the mRNA encoding LHX8, a protein that contains a Lim homeodomain required for the transition from primordial to primary follicle (Pangas et al., 2006).

Many studies have shown that hormones from the hypothalamic-pituitary-gonadal axis, which are essential for sexual maturation and reproductive function in mammals, are also involved in the regulation of some miRNAs. Gonadotropin-Releasing Hormone (GnRH) stimulates the synthesis and the secretion of the pituitary gonadotropins Luteinizing hormone (LH) and Follicle Stimulating Hormone (FSH) that then regulate the production of gonadal steroids and gametogenesis (Conn et al., 1994; Kaiser et al., 1997). GnRH also induces the expression of multiple miRNAs, particularly miR-132 and miR-212, which are encoded by the same gene that is induced by GnRH (Godoy et al., 2011). LH acts on ovarian granulosa cells to induce ovulation and luteinization, resumption of oocyte meiosis and cumulus cell expansion that are crucial steps for adequate ovulation. Moreover, LH acts as a survival factor by preventing apoptosis of granulosa cells (Robker et al., 1998; Chaffin et al., 2001). Interestingly, LH also up-regulates miR-132, miR-212 and miR-21 in mural granulosa cells (Fiedler et al., 2008). MiR-21 is overexpressed in many tumors, including breast, pancreatic, colorectal and oesophageal cancer, and thus is considered as an oncomiRNA (Cho et al., 2007; Verghese et al., 2008; Dillhoff et al., 2008). MiR-21 depletion induces caspase-dependent apoptosis of mouse granulosa cells in vitro and in vivo (Carletti et al., 2010), highlighting the physiological anti-apoptotic role of miR-21 in normal tissues. MiR-200b and miR-429 depletion inhibits LH synthesis by repressing transcription of the gene encoding the subunit of LH. This results in lower serum LH concentration and absence of the LH surge, leading to ovulation failure (Hasuwa et al., 2013). Thus, the hypothalamus-pituitary-ovarian axis requires miR-200b and miR-429 to ensure ovulation. Finally, miR-122 is involved in the down-regulation of LH receptor expression by increasing the expression of LH receptor mRNA Binding Protein (LRBP) via activation of SREBPs (Azhar et al., 2013; Menon et al., 2013).

FSH has a crucial role both in follicle development and granulosa cell proliferation and differentiation. Several miRNAs, including miR-143, miR-125b, miR-21 and the let-7 family, are involved in follicular development in the mouse (Yao et al., 2009). The expression of these RNAs is very low in primordial follicles, but they become readily detectable in granulosa cells of primary, secondary and antral follicles. MiR-143, let-7a and miR-15b are negatively regulated by FSH (Yao et al., 2009). Moreover, miR-133b is involved in FSH-induced estrogen production, by binding to the 3'UTR of Foxl2 and thus reducing FOXL2 protein level in granulosa cells (Dai et al., 2013). FOXL2 is expressed in the ovaries and is necessary for granulosa cell function (Schmidt et al., 2004), particularly through regulation of steroidogenesis genes, including StAR and CYP19A1 that are essential for promoting estradiol production (Pisarska et al., 2011; Caburet et al., 2012).

The implication of miRNAs in the hormonal regulation during folliculogenesis and in the oocyte-niche crosstalk could be exploited for identifying new non-invasive biomarkers of fertility. Moreover, the development of therapies that block the expression or mimic the functions of specific miRNAs could represent a new therapeutic strategy for many gynecological disorders. Similarly, cell-free DNA (cfDNA) molecules, which are released mostly by apoptotic or necrotic cells, are also found in fluids and can be used as biomarkers of pathological conditions (Schwarzenbach et al., 2011). Indeed, cfDNA has been detected in human semen (Chou et al., 2004). This cell-free seminal DNA contains DNA epigenetic information that is essential for proper spermatogenesis (Wu et al., 2013). Circulating cfDNA in the bloodstream is also used to detect gynecological abnormalities and fetal cfDNA in maternal blood constitutes a non-invasive biomarker for fetal aneuploidy (Lo et al., 1999; Bischoff et al., 2002; Bischoff et al., 2005; Bauer et al., 2006; Lo et al., 2008; Wright et al., 2009; Lambert-Messerlian et al., 2013). Recently, it was reported that increased plasma cfDNA levels are associated with low pregnancy rates in IVF programs (Czamanski-Cohen et al., 2013). However, the only correlation was between cfDNA and pregnancy outcome, once the patient was pregnant.

There is no known method for assessing the ovarian reserve of individual patient, therefore determination of ovarian reserve is important in the treatment of infertility.

SUMMARY OF THE INVENTION

The present invention relates generally to the fields of reproductive medicine. More specifically, the present invention relates to methods and kits for determining the ovarian reserve and ovarian function by determining the level of the cell free nucleic acids in the nucleic acid extraction.

DETAILED DESCRIPTION OF THE INVENTION

The inventors studied the relationship between circulating nucleic acid (cell-free DNA and microRNAs) levels in woman serum/plasma and ovarian reserve/function parameters and IVF outcomes. The inventors demonstrate that the analysis of said cell-free nucleic acids in the serum or plasma is informative about ovarian reserve, functions and IVF outcomes. Moreover, the inventors demonstrate that the analysis of said cell-free nucleic acids level in serum or plasma may be used as a non-invasive method for assessing ovarian reserve, functions and IVF outcomes predictions and could represent therapeutic targets to improve ART success.

The inventors also demonstrated miRNA differential expression in follicular fluid samples from women with PCOS and LFOR compared to women with normal ovarian reserve. The inventors also demonstrated differential expression of follicular fluid miRNAs according to the gonadotropin treatment and ovarian response.

Accordingly, the present invention relates to an in vitro non invasive method for determining ovarian reserve in a patient in need thereof comprising the steps consisting of i) providing a biological sample, ii) extracting the cell free nucleic acids from the biological sample and iii) determining the level of the cell free nucleic acids in the nucleic acid extraction.

In some embodiments, the present invention relates to an in vitro non invasive method for determining ovarian reserve in a patient in need thereof comprising the steps consisting of i) providing a serum sample, ii) extracting the cell free nucleic acids from the serum sample and iii) determining the level of the cell free nucleic acids in the nucleic acid extraction.

In some embodiments, the present invention relates to an in vitro non invasive method for determining ovarian reserve in a patient in need thereof comprising the steps consisting of i) providing a follicular fluid sample, ii) extracting the cell free nucleic acids from the follicular fluid sample and iii) determining the level of the cell free nucleic acids in the nucleic acid extraction.

The term "ovarian reserve" has its general meaning in the art and refers to the capacity of the ovary to provide oocytes or ovarian follicles that are capable of fertilization resulting in a healthy and successful pregnancy. With advanced maternal age the number of oocytes or ovarian follicles that can be successfully recruited for a possible pregnancy declines, constituting a major factor in the inverse correlation between age and female fertility.

The term "biological sample" refers to blood, serum, plasma, individual follicular fluid or follicular fluid sample from individual pre-ovulatory follicles. In one embodiment, the term "biological sample" refers to blood, serum, or plasma sample obtained at day 3 of the natural cycle.

The method of the invention is applicable preferably to women but may be applicable to other mammals (e.g., primates, dogs, cats, pigs, cows, mouse . . . ).

As used herein the term "nucleic acid" has its general meaning in the art and refers to refers to a coding or non coding nucleic sequence. Nucleic acids include DNA (deoxyribonucleic acid) and RNA (ribonucleic acid). Example of nucleic acid thus include but are not limited to DNA, mRNA, tRNA, rRNA, tmRNA, miRNA, piRNA, snoRNA, and snRNA. The term "nucleic acid" also relates to circulating miRNA confined within exosomes). According to the invention, the term "nucleic acid" refers to nucleic acids present in the blood, serum, plasma or follicular fluid sample. The term "nucleic acid" also relates to nucleic acids originate from the ovary or ovarian follicules that might go into the blood circulation.

Any methods well known in the art may be used by the skilled artisan in the art for extracting the cell free nucleic acid from the prepared sample. For example, the method described in the example may be used.

In a particular embodiment the method of the invention comprises the steps consisting of i) determining the level of the cell free nucleic acid in the nucleic acid extraction, ii) comparing the level determined at step i) with a reference value, and iii) concluding that the patient have high ovarian reserve when the level determined at step i) is lower than the reference value, and concluding that the patient have low ovarian reserve when the level determined at step i) is higher than the reference value.

In a particular embodiment, the reference value is a threshold value or a cut-off value that can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. Preferably, the person skilled in the art may compare the nucleic acid levels (obtained according to the method of the invention) with a defined threshold value. In one embodiment of the present invention, the threshold value is derived from the nucleic acid levels (or ratio, or score) determined in a blood, serum or plasma sample derived from one or more patients undergoing IVF or ISCI. Furthermore, retrospective measurement of the nucleic acid levels (or ratio, or scores) in properly banked historical blood, serum or plasma samples of patients undergoing IVF or ISCI may be used in establishing these threshold values.

In a particular embodiment, the reference value is 0.4 ng/μl.

Determination of the level of the nucleic acid can be performed by a variety of techniques well known in the art. In a particular embodiment, quantitative PCR may be performed for determining the level of DNA such as described in El Messaoudi et al., 2013; Mouliere et al., 2013; Thierry et al., 2013; Umetani et al., 2006 and WO2012/028746. In particular, the determination of the level of the nucleic acid may be performed by ALU-qPCR and techniques described in the examples.

In some embodiments, the present invention relates to an in vitro non invasive method for determining ovarian function and disorders in a patient in need thereof comprising the steps consisting of i) providing a biological sample, ii) extracting the cell free nucleic acids from the biological sample and iii) determining the level of the cell free nucleic acids in the nucleic acid extraction.

In a particular embodiment the method of the invention comprises the steps consisting of i) determining the level of the cell free nucleic acid in the nucleic acid extraction, ii) comparing the level determined at step i) with a reference value, and iii) concluding that the patient have normal ovarian function and is not afflicted with ovarian disorders when the level determined at step i) is lower than the reference value, and concluding that the patient have abnormal ovarian function and is afflicted with ovarian disorders when the level determined at step i) is higher than the reference value.

The term "ovarian disorders" has its general meaning in the art and relates to diseases selected from by not limited to ovarian cancer, polycystic ovary syndrome (PCOS), premature ovarian failure (POF), low function ovarian reserve (LFOR) and gynecological disorders well known in the art.

In a further aspect of the present invention, the levels of miRNAs are measured.

As used herein, the term "miR" has its general meaning in the art and refers to the miRNA sequence publicly available from the data base http://microrna.sanger.ac.uk/sequences/.

Accordingly, the method according to the present invention also comprises the step of determining the level of at least one miRNA selected from the group consisting of miR-30a, miR-140, let7-b, miR-191, miR-320a, miR-21, miR-30d, and miR-574-3p in the nucleic acid extraction.

The method of the invention may further comprise a step consisting of comparing the expression level of at least one miRNA in the nucleic acid extraction with a reference value, wherein detecting differential in the expression level of the miRNA between the nucleic acid extraction and the reference value is indicative of patient ovarian reserve, ovarian function and disorders.

In one embodiment, higher expression level of miR-30a, miR-191 and miR-574-3p and lower expression level of miR-140, let7-b, miR-320a, miR-21 and miR-30d are indicative of a patient having low ovarian reserve, having abnormal ovarian function or afflicted with ovarian disorders.

In one embodiment, lower expression level of miR-30a, miR-191 and miR-574-3p and higher expression level of miR-140, let7-b, miR-320a, miR-21 and miR-30d are indicative of a patient having high or normal ovarian reserve, having normal ovarian function or not afflicted with ovarian disorders.

MiR-30a was significantly overexpressed (p=0.006) and miR-140 and let-7b were down-regulated (p=0.01 for both) in FF pools from women with polycystic ovary syndrome compared to women with normal ovarian reserve. ROC analysis showed that the combination of intra-follicular miR-30a, miR-140 and let-7b levels could discriminate between polycystic ovary syndrome and normal ovarian reserve with a specificity of 83.8% and a sensitivity of 70% (area under the ROC curve, AUC=0.83 [0.73-0.92]; p<0.0001).

Accordingly, higher expression level of miR-30a and lower expression level of miR-140 and let7-b are indicative of a patient having low ovarian reserve and afflicted with polycystic ovary syndrome, and lower expression level of miR-30a and higher expression level of miR-140 and let7-b are indicative of a patient having high or normal ovarian reserve and not afflicted with polycystic ovary syndrome.

FF expression of miR-30a and miR-191 was significantly up-regulated in patients with low functional ovarian reserve compared to women with normal ovarian reserve (p=0.01 for both). Their combination was very sensitive (85.9%) and specific (71.4%) for low functional ovarian reserve identification (AUC=0.84 [0.67-0.86]; p-value<0.0001).

Accordingly, higher expression level of miR-30a and miR-191 are indicative of a patient having low ovarian reserve and afflicted with low functional ovarian reserve, and lower expression level of miR-30a and miR-191 are indicative of a patient having high or normal ovarian reserve and not afflicted with low functional ovarian reserve.

In some embodiments, the method according to the invention may be performed for assessing in vitro fertilization outcome.

The methods of the invention are particularly suitable for assessing the efficacy of an in vitro fertilization treatment. Accordingly the invention also relates to a method for assessing the efficacy of a controlled ovarian hyperstimulation (COS) treatment in a patient comprising:

i) providing from said patient blood, serum, plasma or follicular fluid sample;

ii) determining ovarian function and disorders by performing the method of the invention; and iii) concluding that the patient is a responder or a non-responder to COS treatment.

Then after such a method, the embryologist may adapt the COS treatment duration or perform COS treatment in a responder patient having low cell free DNA level, high ovarian reserve, normal ovarian function and not afflicted with ovarian disorders.

Accordingly, after such a method, COS treatment may not be performed in a non-responder patient having high cell free DNA level, low ovarian reserve, abnormal ovarian function and afflicted with ovarian disorders. In said non-responder patient, the embryologist may perform COS treatment when the cell free DNA level decreases by ovarian disorders treatment.

The COS treatment may be based on at least one active ingredient selected from the group consisting of GnRH agonists or antagonists associated with recombinant FSH or hMG.

The term "ovarian disorders treatment" has its general meaning in the art and relates to ovarian disorders treatment undergone by ovarian disorders patients. The term "ovarian disorders treatment" also relates to pre-miRs or anti-miRs molecules to re-establish the right level of microRNAs and low level of cell free DNA in the blood.

The invention also relates to a kit for performing the methods as above described, wherein said kit comprises means for determining the level of the cell free nucleic acids. Typically, the kits include primers, probes, macroarrays or microarrays. The kit may further comprise hybridization reagents or other suitably packaged reagents and materials needed for the particular hybridization protocol, including solid-phase matrices, if applicable, and standards. Alternatively the kit of the invention may comprise amplification primers that may be pre-labelled or may contain an affinity purification or attachment moiety. The kit may further comprise amplification reagents and also other suitably packaged reagents and materials needed for the particular amplification protocol.

The invention will be further illustrated by the following figures and examples. However, these examples and figures should not be interpreted in any way as limiting the scope of the present invention.

FIGURES

FIG. 1: Some microRNAs are associated with infertility biomarkers and biomarkers of ovarian reserve.

Relationship between the serum and follicular fluid levels of specific circulating miRNAs (A. miR30a; B. miR-21; C. miR-191; D. miR-140; E. let-7b; F. miR-320a; G. miR-574-3p) and the concentration of LH, AMH, AFC (Antral follicle count) and ovarian reserve status. miR-474-3p is significatively up-regulated in PCOS. PCOS (polycystic ovary sundrome), OI (ovarian insufficiency) or low functional ovarian reserve.

FIG. 2: Cell-free DNA as biomarker of ovarian reserve

Impact of age and AMH level on cfDNA level in serum samples from women undergoing IVF.

FIG. 3: Cell-free DNA as biomarker of ovarian function

Impact of hormonal levels (FSH, LH and estradiol) on cfDNA level in serum samples from women undergoing IVF.

Figure 4:
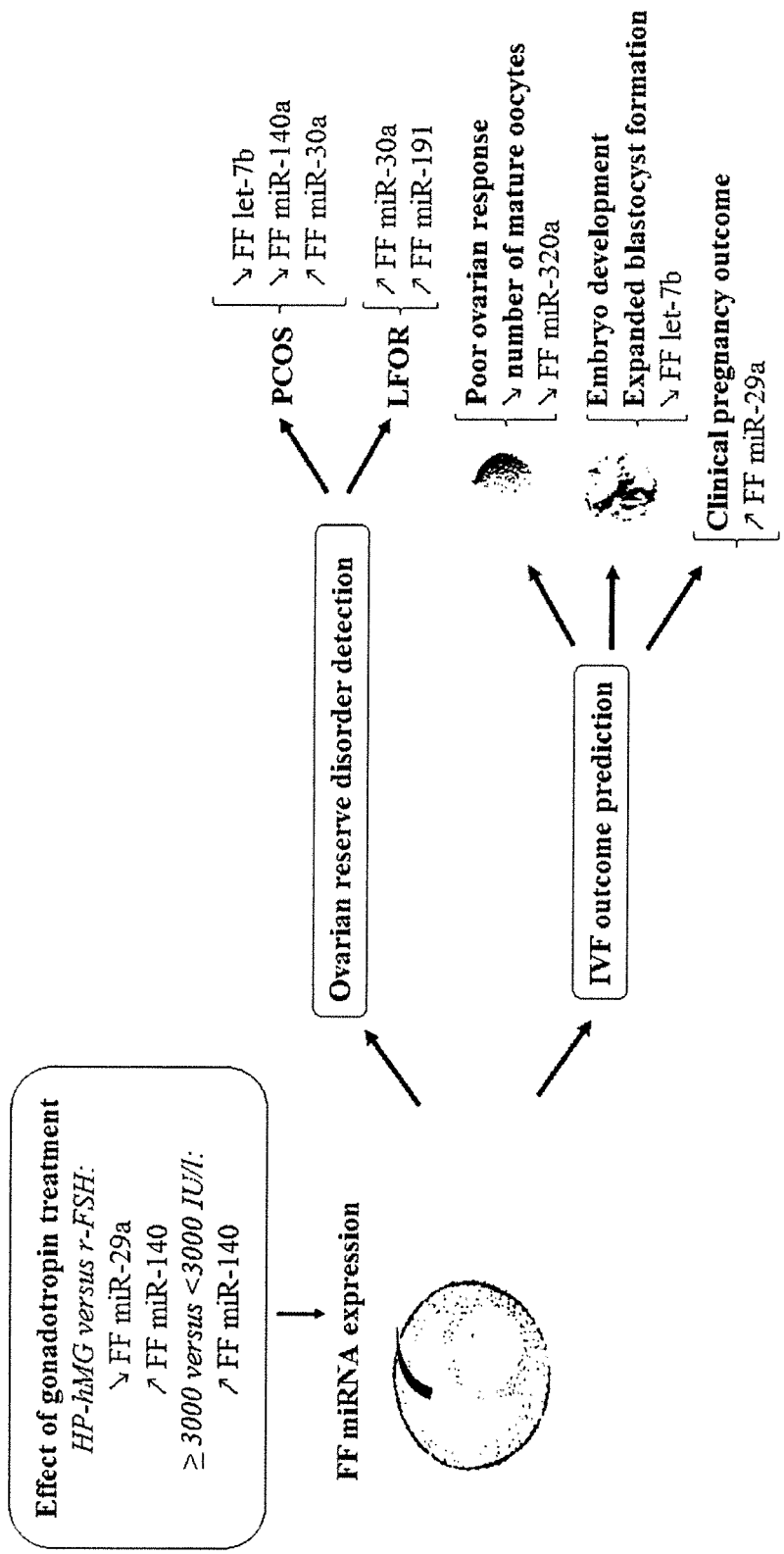

FIG. 4: Schematic model showing that miRNA expression profiling in FF samples provides powerful tools for ovarian reserve disorder detection and IVF outcome prediction during IVF. The expression of some FF miRNAs varies according to the gonadotropin treatment. HPhMG, highly purified human menopausal gonadotropin; r-FSH, follicle-stimulating hormone; PCOS, polycystic ovary syndrome; LFOR, low function ovarian reserve.

Figure 5:
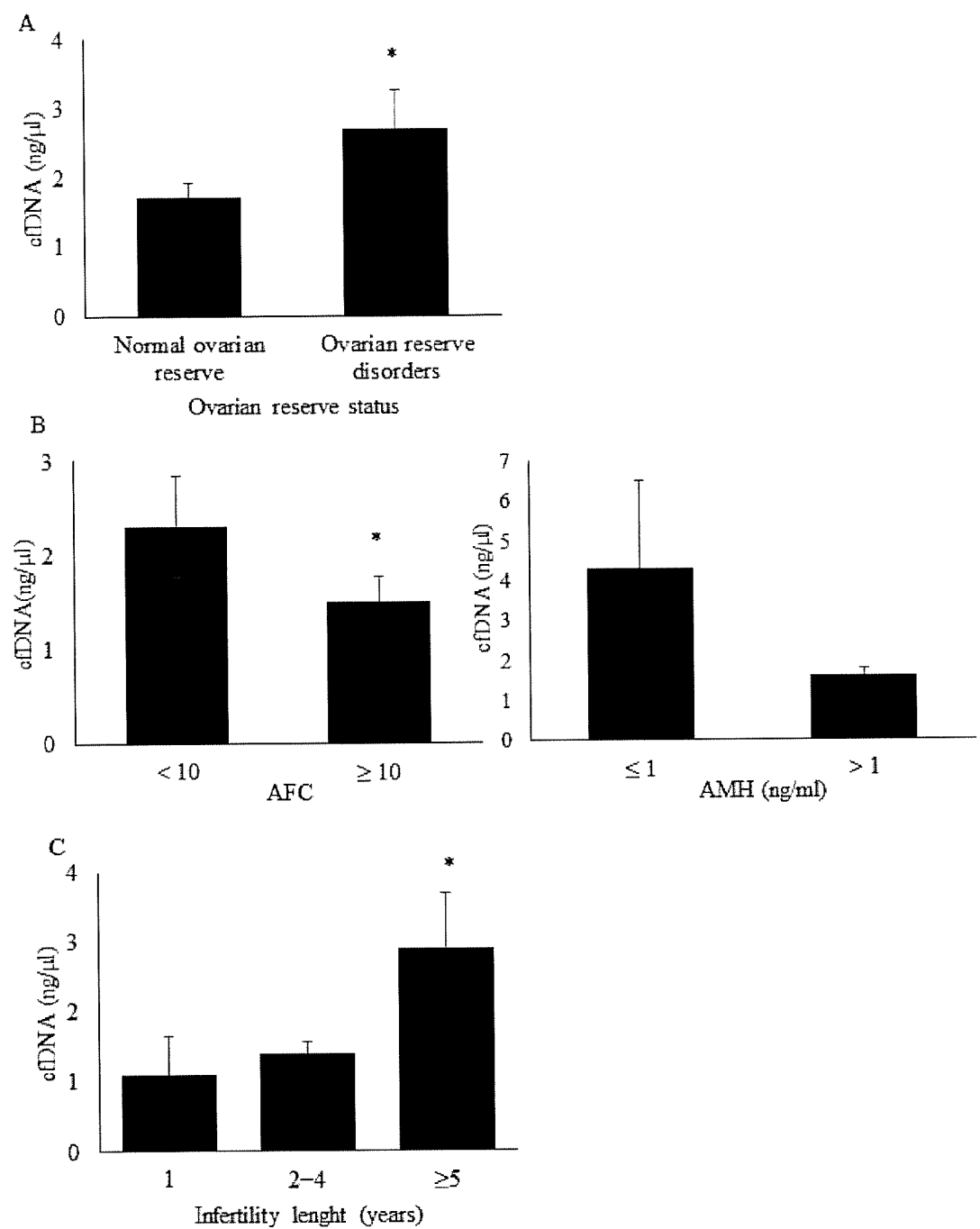

FIG. 5: Cell-free DNA level in follicular fluid (FF) pools according to the patients' ovarian reserve status, ovarian reserve parameters and infertility length. A, FF intra-follicular cfDNA content in patients with normal ovarian reserve versus patients with ovarian reserve disorders (ovarian insufficiency and polycystic ovary syndrome); *p=0.03. B, FF cfDNA content according to the ovarian reserve parameters; left panel: AFC (<10 versus ≥10, *p=0.04); right panel: AMH (≤1 versus >1 ng/ml. *p=0.06). C, FF cfDNA levels according to the infertility length (1 versus ≥5 years, *p=0.049).

Figure 6:
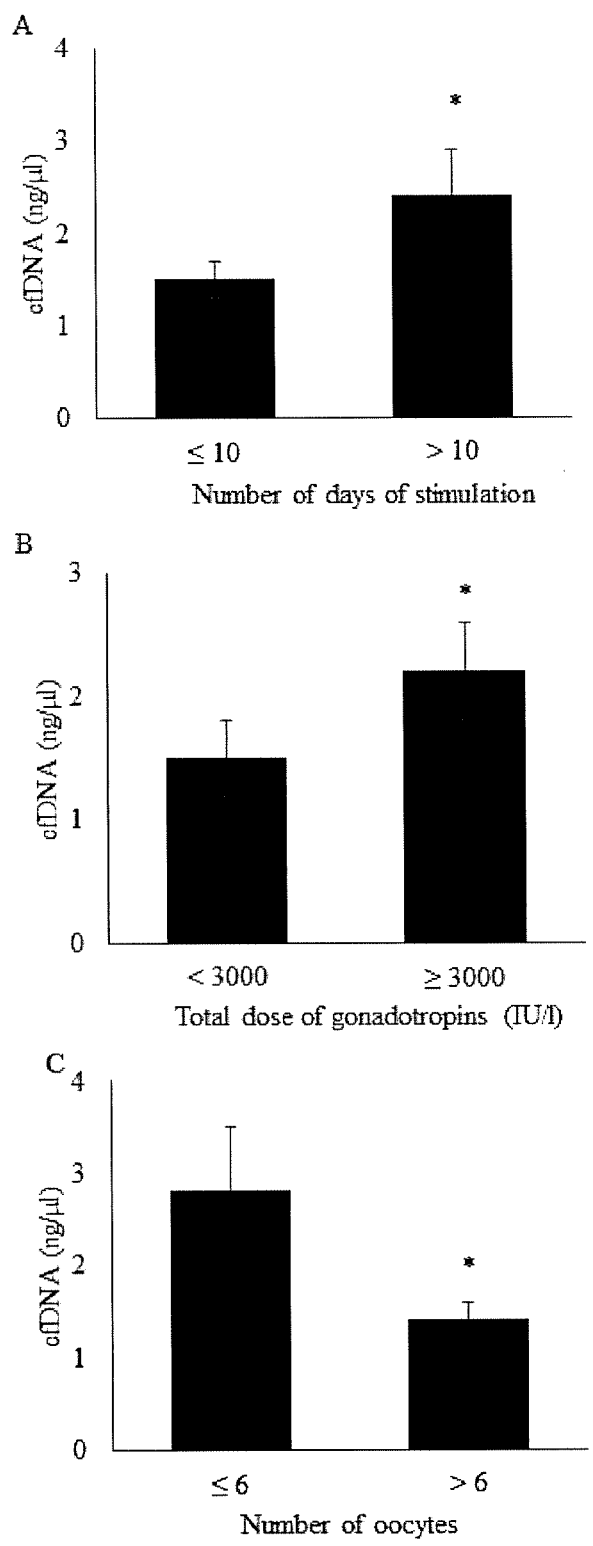

FIG. 6: CfDNA level in follicular fluid pools according to the ovarian stimulation protocol and ovarian response. A, FF cfDNA content according to the length of ovarian stimulation (≤10 versus ≥10 days), *p=0.008. B, FF cfDNA content according to the total dose of gonadotropins (<3000 versus ≥3000 IU/l, *p=0.01). C, FF cfDNA content according to the number of retrieved oocytes (≤6 versus >6 oocytes, *p=0.045).

Figure 7:
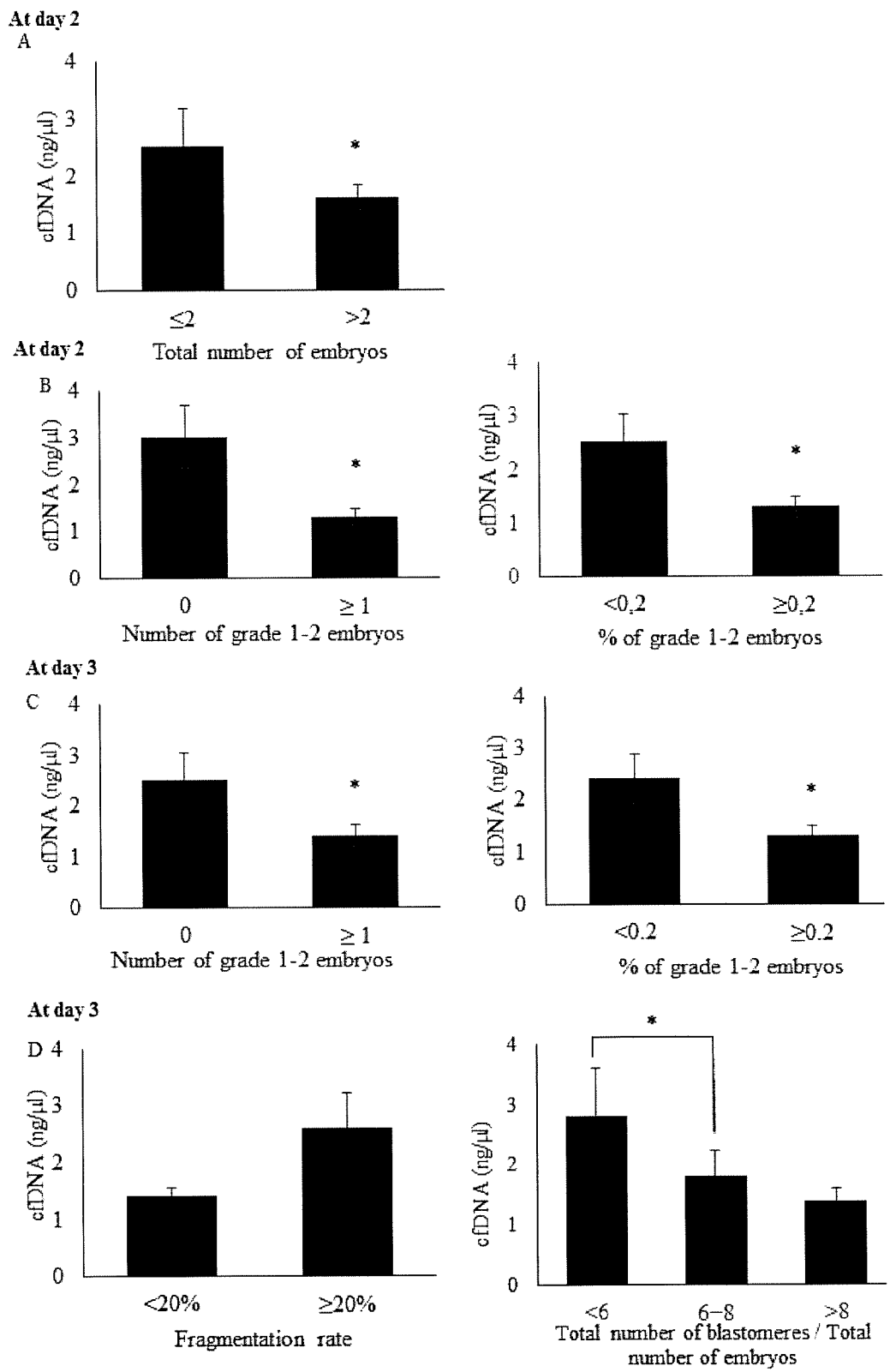

FIG. 7: CfDNA level in follicular fluid pools according to the embryo outcome at day 2 and 3. A, FF cfDNA content according to the total number of embryos at day 2 (≤2 versus >2, *p=0.03). B, FF cfDNA content according to, left panel: the number of top quality (grade 1-2) embryos per patient (0 versus ≥1, *p=0.002) at day 2, right panel: ratio between number of top quality embryos and total number of embryos (<0.2 versus ≥0.2, *p=0.04) at day 2. C, FF ctDNA content according to, left panel: number of top quality (grade 1-2) embryos per patient (0 versus ≥1, *p=0.006) at day 3, right panel: ratio between number of top quality embryo and total number of embryos (<0.2 versus ≥0.2, *p=0.02) at day 3. D, FF cfDNA content according to, left panel: fragmentation rate at day 3 (<20% versus ≥20%, p=0.18) and right panel: ratio between blastomere number and total embryo number at day 3 (<6 versus 6-8, *p=0.02).

Figure 8:
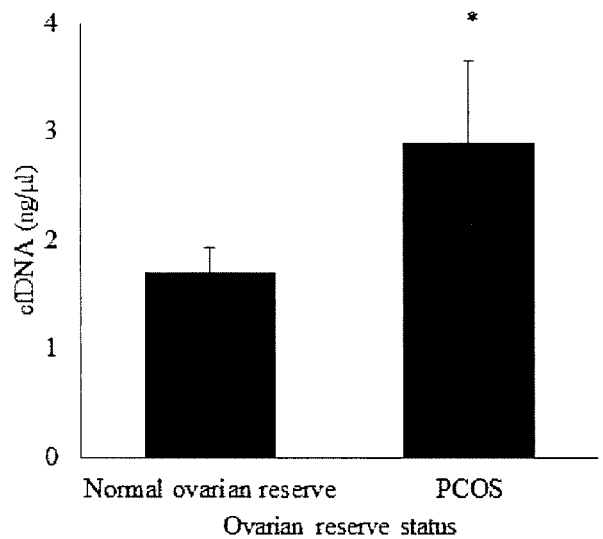

FIG. 8: Comparison of cfDNA levels in follicular fluid pools of patients with normal ovarian reserve (n=94) and patients with polycystic ovary syndrome (PCOS) (n=17); *p=0.049.

Figure 9:
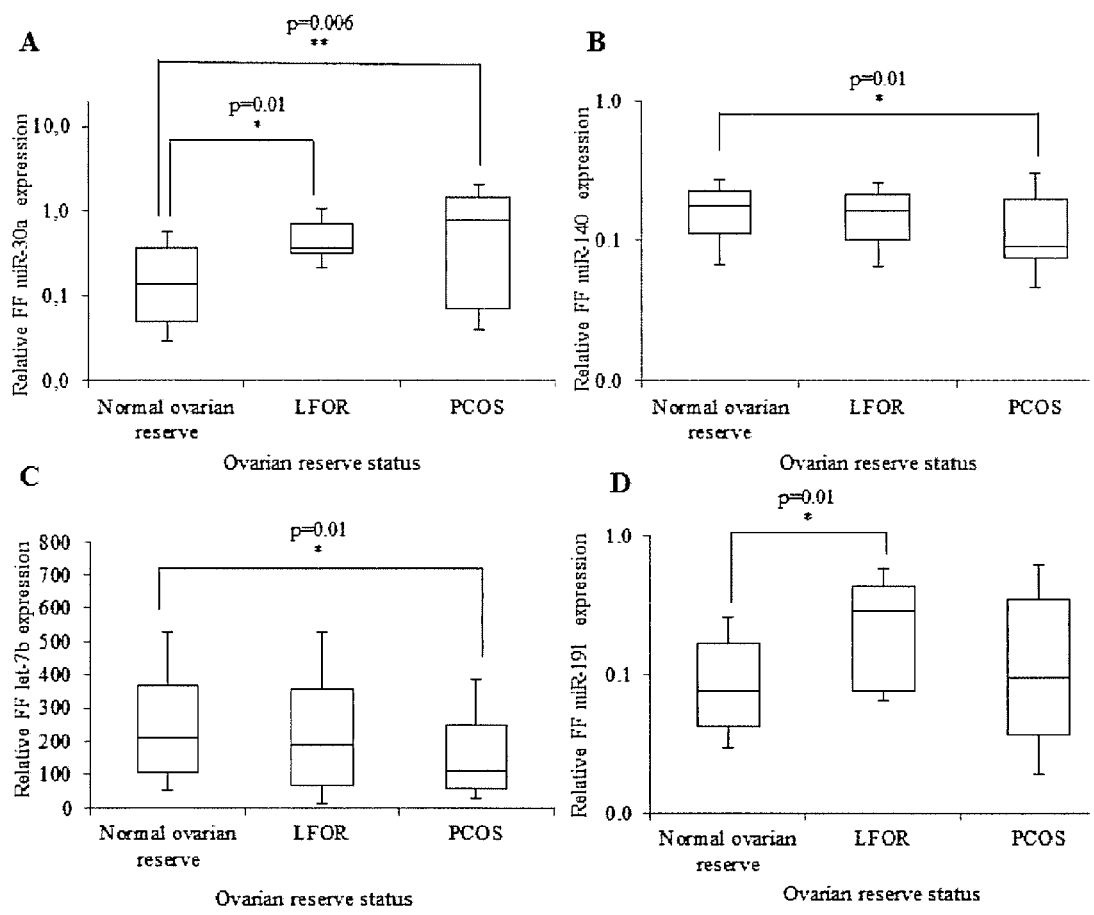

FIG. 9: Comparison of the relative miRNA expression in follicular fluid (FF) pools from women with different ovarian reserve status (normal ovarian reserve, polycystic ovary syndrome (PCOS) and low function ovarian reserve (LFOR)). A, FF miR-30a; B, FF miR-140; C, FF let-7b; D, FF miR-191.

Figure 10:
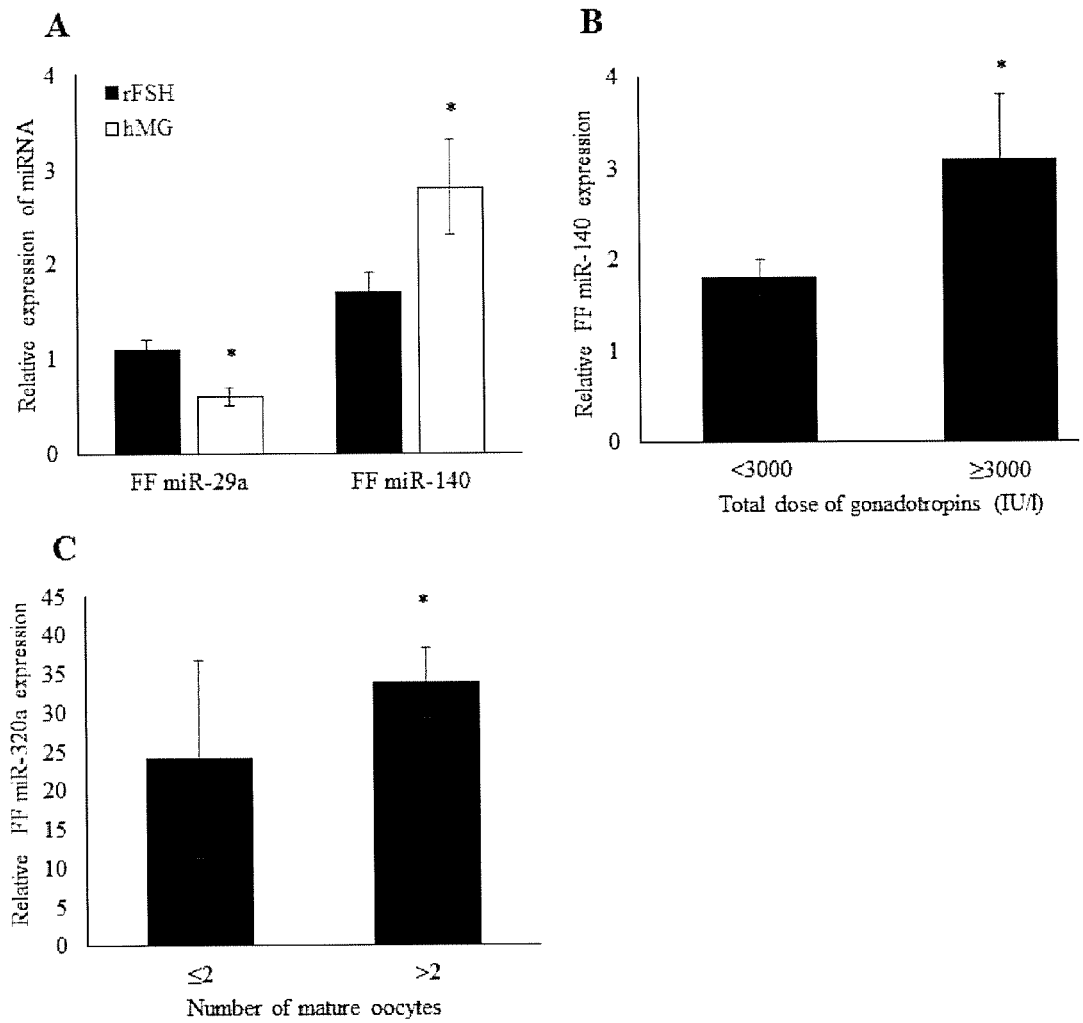

FIG. 10: A, Comparison of FF miR-29a and miR-140 expression level relative to the type of treatment (highly purified human menopausal gonadotropin, hMG, versus recombinant follicle-stimulating hormone, r-FSH). B, Differential FF miR-140 expression according to the total dose of gonadotropins (<3000 versus ≥3000 IU/l). C, Comparison of FF miR-320a expression level relative to the number of retrieved mature oocytes (≤2 versus >2 mature oocytes).

Figure 11:
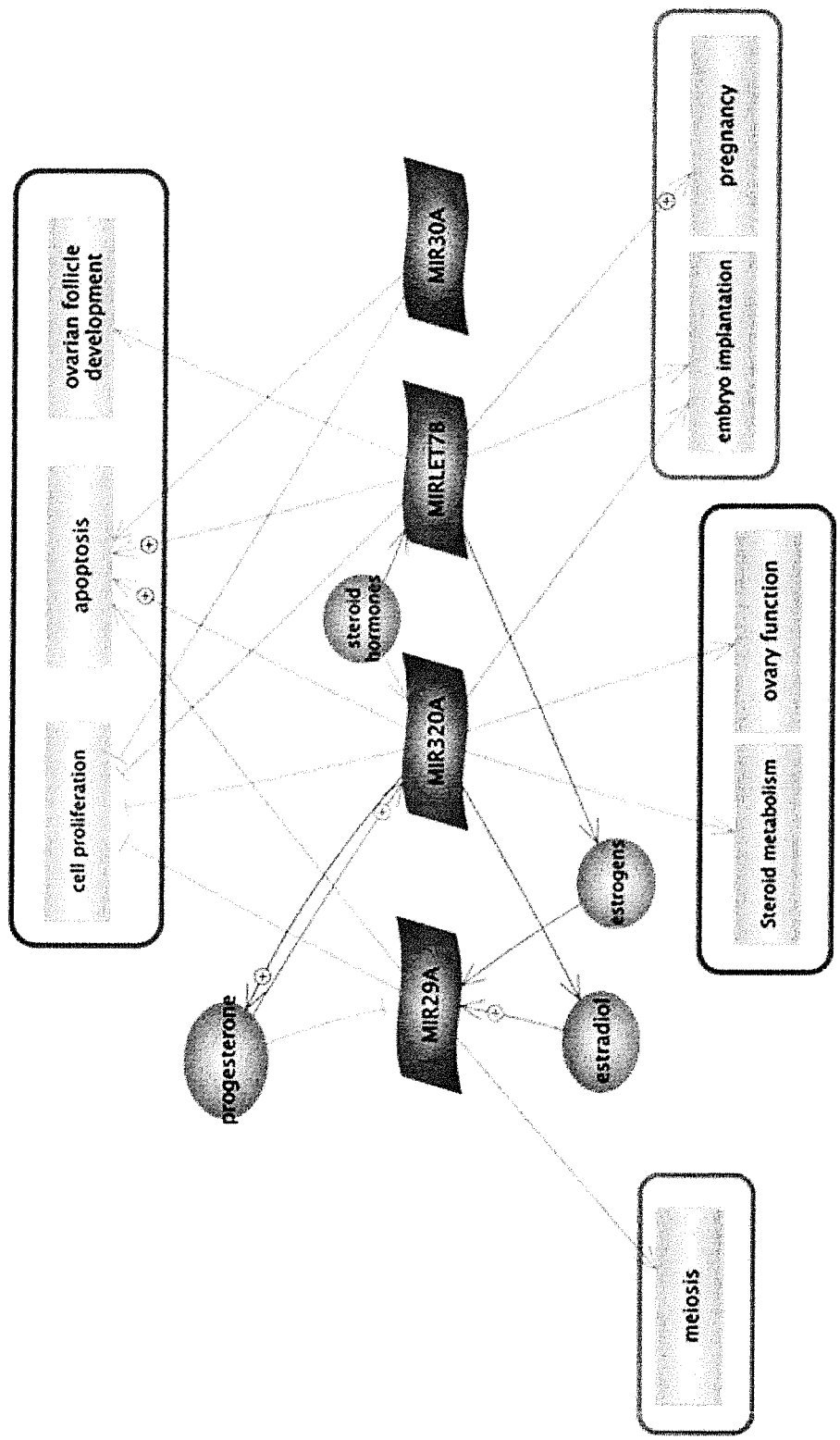

FIG. 11: Pathways involved in reproductive processes and including the circulating miRNAs miR-29a, miR-320a, let-7b and miR-30a, and their interaction with steroid hormones.

FIG. 12: CfDNA quantification at day 3 of menstrual cycle in serum samples from 92 women. Mean±SD=0.25±0.14. A. Correlation between cfDNA serum level and ovarian reserve status—cfDNA level in serum was significantly higher in women with LFOR compared to women with normal ovarian reserve (p=0.045). cfDNA level in serum tended to be higher in women with PCOS compared to women with normal ovarian reserve (p=0.05). Mean (all patients)=0.25±0.4; Mean for normal ovarian reserve=0.19±0.27. B. ROC curves showing the predictive value of cfDNA in LFOR and PCOS—At day 3 of menstrual cycle, cfDNA level in serum predicted significantly LFOR (AUC=0.64; Se=52%; SP=75%; cutoff>0.17). At day 3 of menstrual cycle, cfDNA level in serum predicted significantly PCOS (AUC=0.65; Se=95%; SP=34%; cut-off>0.06). C. Correlation between cfDNA serum level and age—cfDNA level in serum was significantly higher in older women (age>36 ou age≥36 years) compared to young women (age<36 or age≤36 years) (p=0.037; p=0.024, respectively). D. Correlation between cfDNA serum level at day 3 of menstrual cycle and age—cfDNA level in serum at day 3 of menstrual cycle was significantly and positively correlated with women's age (r=0.27; p=0.02). E. Correlation between cfDNA serum level in women undergoing IVF/ICSI procedure (n=26) and oocyte number. At day 3 of menstrual cycle, cfDNA level was significantly higher in serum samples from women who obtained less than 6 oocytes at oocyte day (≤6 oocytes) compared to those who obtained more than 6 oocytes (>6 oocytes) (p=0.013). cfDNA level at day 3 of menstrual cycle could predict the number of retrieved oocyte and thus IVF/ICSI prognosis. Spearman correlation+++: r=−0.42; p=0.03. F. Correlation between cfDNA serum level in women undergoing IVF/ICSI procedure (n=26) and oocyte number. cfDNA level in serum was significantly and negatively correlated with the number of retrieved oocyte during IVF/ICSI procedure (r=−0.42; p=0.03). cfDNA level at day 3 of menstrual cycle could predict the number of retrieved oocyte and thus IVF/ICSI prognosis. G. Correlation between cfDNA and AMH serum levels—For Patients with normal ovarian reserve and with LFOR (PCOS were excluded from this analysis). Comparison with AMH level at day 3 of menstrual cycle, classical biomarker, used to assess ovarian reserve. At day 3 of menstrual cycle, cfDNA level was significantly higher in serum samples from women with AMH≤1 ng/ml or ≤2 ng/ml compared to those with AMH>1 ng/ml or >2 ng/ml, respectively (p=0.046; p=0.004, respectively). H. Correlation between cfDNA and AMH serum levels at day 3 of menstrual cycle—cfDNA level in serum at day 3 of menstrual cycle was significantly and negatively correlated with AMH level in serum at day 3 of menstrual cycle (r=−0.32; p=0.006). I. Correlation between cfDNA and AMH serum levels—All patients were included in this analysis (n=92). Comparison with AMH, classical biomarker, used to assess ovarian reserve. At day 3 of menstrual cycle, cfDNA level was significantly higher in serum samples from women with AMH≤2 ng/ml compared to those with AMH between 2 and 5 ng/ml (p=0.013). At day 3 of menstrual cycle, cfDNA level tended to be higher in serum samples from women with AMH≥5 ng/ml compared to those with AMH between 2 and 5 ng/ml (p=0.09).

FIG. 13: MicroRNAs expression at day 3 of menstrual cycle in serum samples from 70 women. A. Correlation between Let-7b expression and age—Let-7b expression in serum was higher in older women (age≥38 years) compared to women aged less than 38 years old. Comparison microRNA expression profiles and LH at day 3 of menstrual cycle, used to assess ovarian function. B. Correlation between MiR-30d, miR-320a expression levels and age—MiR-30d, and miR-320a expression decreased significantly in women with high LH levels (>5 IU/l) compared to women normal LH levels (between 3-5 IU/l) (p<0.03; p<0.02; p<0.02, respectively).

EXAMPLES

Example 1

The present invention relates to a non-invasive method for predicting the ovarian reserve/functions of a woman, IVF outcomes, and the use of these new biomarkers as therapeutic targets in order to improve ART success.

This invention comprises the steps consisting of:
i) Providing a sample of serum or plasma,
ii) extracting the cell-free nucleic acids (cell-free DNA and microRNAs) from the sample,
iii) determining the level of the cell-free nucleic acids (cell-free DNA and microRNAs) in the nucleic acid extractions
iiii) Treating women with pre-miRs or anti-miRs molecules to re-establish the right level of microRNAs in the blood.

Several studies have shown that miRNAs are involved in intercellular signaling (Valadi et al., 2007). Indeed, miRNAs can be secreted in the extracellular medium by donor cells to act on other cells. These circulating miRNAs are protected from degradation in small vesicles called exosomes and can be found in biological fluids, such as serum or plasma. In order to identify the miRNAs that are implicated in the CC-oocyte crosstalk and that regulate key genes implicated in folliculogenesis and ovarian function, we analyzed by deep sequencing the miRNAs present in mature MII oocytes and in the associated CCs (Assou et al., 2013). Only three miRNAs were found to be expressed in oocytes (miR-184, miR-100 and miR-10a) and 32 in CCs. Among the miRNAs expressed in CCs, we selected some based on their possible involvement in folliculogenesis and investigated whether they could be detected also in serum samples from women who were undergoing IVF by using quantitative RT-PCR (RT-qPCR).

Material & Methods

Patients and Serum Samples

This prospective study included 70 women consulting for infertility problems in the laroboratory EYLAU-UNILABS in Paris. Written informed consent was obtained for the use of serum samples at Day 3 of the natural cycle. The women's age ranged from 23 to 47 years. The baseline hormonal status was evaluated in each patient at day 3 of the cycle.

Serum Sample Collection

Blood samples were collected in serum separator tubes and centrifuged to separate blood cells from serum. Serum was then filtered and stored a −80° C. until nucleic acid extraction.

MiR Extraction and Quantification

MicroRNAs were extracted from serum samples with the QIAamp circulating nucleic acid kit from QIAGEN and then they were quantified by quantitative real-time RT-PCR, using the TaqMan technology. Taqman provides pre-formulated stem-loop primers designed for each miRNA. For real time PCR, a fluorogenic probe was used to enable the detection of the specific PCR product as it accumulates during the PCR cycles.

Cell-Free DNA Extraction and Quantification

Quantification of cell-free DNA in serum samples from infertile women undergoing IVF was performed by quantitative real-time PCR of ALU repeats using an already published primer set (ALU115) (Umetani et al., 2006). 20 µl of each serum sample was mixed with 20 µl of a buffer containing 25 ml/l Tween 20, 50 mmol/l Tris and 1 mmol/l EDTA and then digested with 16 µg of proteinase K (PK) (Qiagen) at 50° C. for 20 minutes followed by heat-inactivation and insolubilisation at 95° C. for 5 min. Samples were then centrifuged at 10,000 g for 5 min and supernatants collected and stored at −80° C. until cfDNA quantification. CfDNA was quantified by qPCR for human ALU repeats using two primer sets that generate a 115-bp amplicon (ALU115 primers) and a 247-bp amplicon (ALU247 primers), respectively. For each ALU-qPCR, 1 μl of each PK-digested FF sample was added to a reaction mixture (final volume: 10 μl) containing 0.25 μM of forward and reverse primers (ALU115 or ALU247) and 5 μl of 2× LightCycler®480 SYBR Green I master mix (Roche Applied Science, Germany). Serum cfDNA concentrations were calculated based on a standard curve prepared with successive dilutions of genomic DNA. A negative control (without template) was added in each qPCR plate. All measures were performed in quadruplicate.

Results

Some microRNAs Found in Cumulus Cells are Present in Serum

Quantitative real-time RT-qPCR analysis of miR-21 expression in cumulus cells (CC) and serum samples from infertile women.

For example, miR-21 can be measured both in CCs and in serum. Many other miRs are present both in serum and in cumulus cells and other are present both in follicular fluid (or ovary in general) and serum and could represent good candidates for biomarkers.

Some microRNAs are Associated with Infertility Biomarkers

Relationship between the serum level of specific circulating miRNAs and the concentration of LH, AMH, cfDNA and the BMI. The level of miR-30d, -320a, -21, -125a, -191 and let-7b, which are expressed in cumulus cells, was quantified in serum samples from infertile women. The serum levels of miR-30d and miR-320a were compared in women with normal (2-5 UI/l) or abnormal (>5 UI/l) LH concentration. miR-21 serum levels were compared in women with low or high cfDNA amounts; let-7b serum levels in women with normal (≥2 ng/l) or low AMH concentration (<2 ng/l). miR-125a and miR-191 serum levels in function of the BMI. The P values were calculated by using the unpaired t-test, using the GraphPad software.

The possible relationships between hormonal markers of ovarian reserve at day 3 of the cycle and circulating miRNA expression were assessed. First, we compared LH level at day 3 with the serum level of miR-30d and miR-320a, which are expressed in CCs in contact with mature MII oocytes. The inventors demonstrated that the level of circulating miR-30d and miR-320a was significantly lower (p=0.02 and 0.01, respectively) in women with high LH (>5 UI/l). Interestingly, miR-30d expression is altered after FSH treatment of rat granulosa cells in culture (Yao et al., 2010), suggesting that these miRNAs could be regulated by at least two gonadotropin hormones (LH and FSH). Our finding of a negative correlation between miR-320a and LH levels might provide an explanation for the miR-320a decrease in the follicular fluid observed in patients with PCOS (Sang et al., 2013). Anti-Müllerian hormone (AMH), which is expressed by granulosa cells and controls the formation of primary follicles by inhibiting excessive follicular recruitment by FSH (Weenen et al., 2004), is a marker of ovarian reserve, PCOS and premature ovarian failure (Visser et al., 2006). Moreover, AMH level is commonly used to predict the ovarian response during IVF procedures (Broer et al., 2013). Our data shows that circulating let-7b is increased in serum samples from women with low AMH levels (<2 ng/ml). This miRNA is also expressed in bovine COCs, suggesting a major role in oocyte-CC crosstalk (Miles et al., 2012). Another report highlighted a role of let-7b in oocyte meiotic competence and maturation (Kim et al., 2013). Our preliminary data suggest that let-7b might provide a new non-invasive prognostic tool before an IVF procedure. We also investigated the possibility that high cfDNA levels could influence miRNA expression in the serum. The inventors also found that miR-21 was significantly under-expressed in serum samples from patients with relatively high levels (>0.4 ng/μl of serum) circulating cfDNA (p=0.03) (Umetani et al., 2006). As miR-21 depletion leads to granulosa cell apoptosis (Carletti et al., 2010), it could explain the increased cfDNA release in the serum and by default the ovarian apoptosis. Thus, this event might be detected in the blood by quantifying the circulating cfDNA.

A high body mass index (BMI) can be considered as an indicator of female infertility and deregulation of some miRNAs has been implicated in obesity. We thus compared the circulating levels of miRNAs expressed in CCs and the BMI of the patients and found a dramatic decrease of the serum level of miR-125a and miR-191 when BMI>25 (p=0.001 for both). These miRNAs have never been related to obesity or infertility, although miR-191 was reported to be expressed in follicular fluid (Sang et al., 2013).

These preliminary results suggest that circulating microRNAs represent a yet unexplored tool for the diagnosis/monitoring of infertility/ovarian response.

Comparison Expression miRs and Biomarkers of Ovarian Reserve:

Likewise, the inventors detected significant variations of follicular fluid (FF) miRNA levels by comparing their expressions to classical biomarkers of ovarian reserve, serum AMH level and AFC at day 3 of the menstrual cycle, divided into three groups (ie, AMH level: <1, 1-3, >3 ng/ml; AFC: <10, 10-19, >19). These cut-offs were defined based on some previously published works (Ficicioglu et al., 2014; Ocal et al., 2011; Jayaprakasan et al., 2010; Lauritsen et al., 2014).

Indeed, FF miR-30a levels were significantly higher in women with very low serum AMH concentration (<1 ng/ml) than in those with normal AMH level (comprised between 1-3 ng/ml) (p=0.03) (FIG. 1A, left panel). Similarly, FF miR-191 tended to increase in patient's group with low AMH levels compared to group with normal AMH levels (p=0.13) (FIG. 1B, left panel). The expression of miR-140 decreased significantly in FF pools from women's group with higher serum AMH levels (>3 ng/ml) compared to women with normal AMH levels (p=0.007) (FIG. 2C, left panel). As FF miR-140, FF let-7b levels tended to be lower in women with elevated serum AMH levels than those with normal AMH levels (p=0.07) (FIG. 1D). Moreover, FF miR-30a and miR-191 were significantly and highly expressed in women with low AFC (<10) compared to those with AFC included between 10 and 19 (p=0.03; p=0.02, respectively) (FIGS. 1A and 1B, right panels). Significant decreased miR-140 expressions were also observed in FF pools from patients with high AFC (>19) compared to women with AFC comprised between 10 and 19 (p=0.04) (FIG. 1C, right panel). Likewise, by using Spearman's Rank correlation calculation, we found significant and negative correlations between FF miR-140 expression, and serum AMH levels and AFC, respectively (r=−0.19; p=0.04; r=−0.29, p=0.003, respectively).

In addition, after comparing FF miRNA expressions and the other potential biomarkers, reflecting ovarian function (ie, FSH, LH, E2 levels at day 3 of menstrual cycle), we found that FF miR-320a levels were significantly and negatively correlated to basal LH rates in serum (r=−0.18; p=0.045). Indeed, FF pools related to women with high serum LH levels (>5 IU/l) contained significant low levels of miR-320 expression than women with normal basal LH levels (3-5 IU/l) (p=0.01) (FIG. 1E).

Always in order to identify among FF candidate miRNA, those related to ovarian reserve status, we compared miRNA expressions to classical biomarkers of ovarian reserve (ie AMH and AFC). Among previous miRNA related to PCOS, miR-140 is significantly down-expressed in FF samples from patients with higher AMH levels and AFC, respectively. Moreover, FF let-7b expression levels tended to be lower in FF samples from women with higher AMH levels. Therefore, these observations confirm our previous results, which demonstrated under-expressions of FF miR-140 and let-7b in case of PCOS. Moreover, miR-30a is significantly up-expressed in FF from patients with low AMH levels and AFC, respectively. Likewise, FF miR-191 expression levels tend to be higher for women with low AMH, and were significantly increased for those with low AFC. In addition, these results are in accordance with previous data, reported over-expressions of these two FF miRNAs in ovarian insufficiency (OI) patients.

miR-320a: Recently, several studies reported divergent findings regarding to miR-320a expression levels in FF from women with PCOS (Sang et al., 2013; Roth et al., 2014; Yin et al., 2014). Indeed, Sang et al., showed a significantly lower expression of FF miR-320a in PCOS patient (Sang et al., 2013), although Roth et al., did not identify differential FF miR-320 expression in these patients (Roth et al., 2014). By contrast, Yin et al., found the expression of miR-320 was up-regulated in FF of PCOS patients (Yin et al., 2014). As it was reported by Roth et al., miR-320 expression levels did not differ significantly between PCOS and healthy patients in our cohort. However, we observed that miR-320 expression levels were significantly lower in FF related to women with high basal LH rates. Since in most women with PCOS, serum LH level is commonly increased, this result appears in accordance with previous result, described by Sang, et al.

Likewise, it was established that PCOS is typically characterized by an impaired oocyte maturation, leading to a small number of mature oocytes, collected at oocyte retrieval (Qiao and Feng, 2011).

The inventors also demonstrated that miR-21 expression is associated with ovarian reserve biomarkers. As shown in FIG. 1B, miR-21 is increased in serum samples from women with high AMH levels and high AFC.

As shown in FIG. 1G, miR-574-3p is significantly up-regulated in PCOS patients.

Cell-Free DNA as Biomarker of Ovarian Reserve (FIG. 2)

Impact of age and AMH level on cfDNA level in serum samples from women undergoing IVF. Low AMH concentration is <2 ng/l. CfDNA was measured by quantitative real-time RT-qPCR analysis using ALU primers. The P values were calculated with unpaired t-tests, using the GraphPad software.

CfDNA is released in the circulation following physiological and pathological cell necrosis and apoptosis. Based on the finding that the abundance of cfDNA can change in abnormal situations, we hypothesized that an increase in cfDNA might reflect ovarian reserve disorders. It is expected that an increase of cfDNA level might be correlated with pregnancy outcome. We thus quantified cfDNA in the serum of women candidates for IVF and compared it with age and AMH level in blood. CfDNA level is higher in older patient serum (38 years old and more), than in younger ones. Likewise, serum cfDNA level is higher in women with abnormal AMH level (<2 ng/µl) than in whom with normal AMH level. CfDNA could constitute a new biomarker of ovarian reserve.

Cell-Free DNA as Biomarker of Ovarian Function (FIG. 3)

Impact of hormonal levels (FSH, LH and estradiol) on cfDNA level in serum samples from women undergoing IVF. Normal FSH level=3-9 UI/l; abnormal levels are <3 or >9 UI/l. Normal LH concentration is >2 UI/l and ≤5UI/L. Normal Estradiol (E2) concentration is ≤45 pg/ml and abnormal is >45 pg/ml. CfDNA was measured by quantitative real-time RT-qPCR analysis using ALU primers. The P values were calculated with unpaired t-tests, using the GraphPad software.

CfDNA level has been compared with the level of FSH, LH and Estradiol (E2) at day 3 of the cycle.

Our data suggest that the serum concentration of cell-free nucleic acids could be related to the ovarian hormonal status and functions. These findings suggest that cell-free nucleic acids may be used as non-invasive biomarkers of in vitro fertilization outcome.

Conclusions:

Model on how cell-free nucleic acids could be used as new non-invasive biomarkers of infertility and IVF outcome.

The profiling of circulating nucleic acids, such as microRNAs and cell-free DNA, opens new perspectives for the diagnosis/prognosis of ovarian disorders and for the prediction of in vitro fertilization outcomes (embryo quality and pregnancy).

Due to their accessibility and stability (miRNAs circulate confined within exosomes), different circulating miRNAs could be used, alone or in combination, as non-invasive biomarkers of gynecological cancers and gynecological disorders.

Example 2

Material & Methods

Patients

This prospective study recruited 100 women enrolled in conventional IVF (n=31) or ICSI (n=69) program at the ART-PGD Department of the University Hospital of Montpellier. The patients' characteristics are detailed in Table 1. The women's age was 34.3±4.5 years (mean±SD; range: 23 to 43 years) and the body index mass (BMI) was 23.3±4.2 kg/m$^2$ (mean±SD; range: 17 and 39 kg/m$^2$). The infertility length was 3.5±1.7 years (mean±SD). For 61% of the couples this was the first IVF or ICSI cycle and the remaining 39% of the couples had undergone at least one cycle (mean cycle number±SD: 2.1±1.3). In 11% of the couples, no specific cause of infertility was detected, while in the other couples, male (37%), female (36%) or mixed (16%) factors were identified. Based on the AMH level and AFC at day 3 of menstrual cycle, 94 of the 100 patients had a normal ovarian reserve and 6 had low functional ovarian reserve (LFOR). Basal FSH, LH and E2 levels were quantified also at day 3 of the menstrual cycle in each patient (Table 1).

TABLE 1

CfDNA level in follicular fluid pools according to the patients' clinical characteristics.

| Variable | Mean | n (total = 100) | Min-Max | SD | FF cfDNA (ng/ul) Mean ± SD [95% CI] | p-value |
|---|---|---|---|---|---|---|
| Age (years) | 34.3 | — | 23-43 | 4.5 | — | — |
| <37 years | — | 64 | — | — | 1.9 ± 2.7 [0.1-2.5] | 0.19 NS |
| ≥37 years | — | 36 | — | — | 1.5 ± 1.0 [1.1-1.8] | |
| BMI (kg/m$^2$) | 23.3 | — | 17-39 | 4.2 | — | — |
| 18.5 ≤ BMI < 25 | — | 58 | — | — | 1.9 ± 2.6 [1.2-2.6] | ref |
| BMI < 18.5 | — | 10 | — | — | 1.2 ± 1.1 [0.4-1.9] | 0.54 NS |
| 25 ≤ BMI < 30 | — | 24 | — | — | 1.7 ± 1.6 [1.0-2.4] | 0.56 NS |
| BMI ≥30 | — | 8 | — | — | 1.6 ± 1.5 [0.3-2.8] | 0.93 NS |
| Infertility length (years)* | 3.5 | — | 1-9 | 1.7 | — | — |
| 1 | — | 8 | — | — | 1.1 ± 1.6 [0-2.4] | ref |
| 2-4 | — | 68 | — | — | 1.4 ± 1.3 [1.1-1.7] | 0.08 NS |
| ≥5 | — | 23 | — | — | 2.9 ± 3.8 [1.3-4.5] | 0.049 |
| Infertility aetiology | | | | | | |
| Male factor | — | 37 | — | — | 1.5 ± 1.1 [1.1-1.9] | ref |
| Female factor | — | 36 | — | — | 1.9 ± 2.1 [1.2-2.6] | 0.72 NS |
| Tubal alterations (%) | — | 9 (25) | — | — | 1.3 ± 1.6 [0.1-2.5] | 0.28 NS |
| Endometriosis (%) | — | 21 (58.3) | — | — | 2.1 ± 2.5 [0.9-3.2] | 0.67 NS |
| Ovulatory dysfunction (%) | — | 1 (2.8) | — | — | — | — |
| Ovarian disorders (%) | — | 4 (11.1) | — | — | 2.3 ± 1.3 [0.1-4.4] | 0.28 NS |
| Uterine factor (%) | — | 1 (2.8) | — | — | — | — |
| Mixed infertility | — | 16 | — | — | 1.7 ± 3.1 [0.1-3.4] | 0.08 NS |
| Unexplained infertility | — | 11 | — | — | 2.0 ± 3.7 [0-4.5] | 0.23 NS |
| Primary infertility | — | 61 | — | — | 2.1 ± 2.7 [1.5-2.8] | 0.08 NS |
| Secondary infertility | — | 39 | — | — | 1.1 ± 0.8 [0.8-1.4] | |
| IVF/ICSI cycle number | 2.1 | — | 1-4 | 1.3 | — | — |
| 1 | — | 39 | — | — | 1.2 ± 0.9 [0.9-1.5] | 0.39 NS |
| >1 | — | 61 | — | — | 2.1 ± 2.7 [1.4-2.8] | |
| Baseline evaluation | | | | | | |
| FSH (IU/l)* | 7.4 | — | 0.1-19 | 2.4 | — | — |
| <10 | — | 87 | — | — | 1.6 ± 2.0 [1.2-2.1] | 0.42 NS |
| ≥10 | — | 12 | — | — | 2.4 ± 3.7 [0-4.7] | |
| LH (IU/l)* | 5.7 | — | 1-11.2 | 1.9 | — | — |
| 3-5 | — | 32 | — | — | 1.4 ± 1.3 [0.9-1.8] | ref |
| <3 | — | 5 | — | — | 2.0 ± 1.0 [0.7-3.3] | 0.1 NS |
| >5 | — | 60 | — | — | 1.8 ± 2.6 [1.1-2.4] | 0.7 NS |
| E2 (pg/ml)* | 40.7 | — | 4-99 | 17.8 | — | — |
| ≤45 | — | 66 | — | — | 1.8 ± 2.5 [1.2-2.5] | 0.56 NS |
| >45 | — | 32 | — | — | 1.5 ± 1.6 [1.0-2.1] | |
| AMH (ng/ml)* | 2.7 | — | 0.2-8.6 | 1.6 | — | — |
| ≤1 | — | 5 | — | — | 4.3 ± 5.0 [0-10.4] | 0.06 NS |
| >1 | — | 90 | — | — | 1.6 ± 2.0 [1.2-2.0] | |
| AFC* | 13.7 | — | 3-25 | 5.7 | — | — |
| <10 | — | 24 | — | — | 2.3 ± 2.6 [1.2-3.4] | 0.04 |
| ≥10 | — | 63 | — | — | 1.5 ± 2.2 [1.0-2.1] | |
| Normal ovarian reserve | — | 94 | — | — | 1.7 ± 2.3 [1.3-2.2] | ref |
| Ovarian insufficiency | — | 6 | — | — | 2.1 ± 1.4 [0.6-3.6] | 0.29 NS |
| Agonist protocol** | — | 48 | — | — | 1.4 ± 2.0 [0.9-2.0] | 0.09 NS |
| Antagonist protocol | — | 50 | — | — | 1.8 ± 1.8 [1.3-2.3] | |
| Ovarian stimulation treatment | | | | | | |
| Days of stimulation | 10 | — | 7-14 | 1.2 | — | — |
| 7-10 | — | 71 | — | — | 1.5 ± 1.9 [1.0-1.9] | 0.008 |
| >10 | — | 29 | — | — | 2.4 ± 2.8 [1.4-3.5] | |
| Total dose of gonadotropins (IU/l) | 2414.7 | — | 875-4950 | 932.5 | — | — |
| <3000 | — | 66 | — | — | 1.5 ± 2.1 [1.0-2.0] | 0.01 |
| ≥3000 | — | 34 | — | — | 2.2 ± 2.3 [1.4-3.0] | |
| Agonist protocol | | | | | | |
| Days of stimulation | 10 | — | 8-14 | 1.1 | | |
| 8-10 | — | 37 | — | — | 1.1 ± 1.1 [0.7-1.4] | 0.05 NS |
| >10 | — | 11 | — | — | 2.7 ± 3.6 [0.3-5.1] | |
| Total dose of gonadotropins (IU/l) | 2324 | — | 900-4200 | 797.8 | | |
| <3000 | — | 34 | — | — | 1.1 ± 1.1 [0.7-1.5] | 0.049 |
| ≥3000 | — | 14 | — | — | 2.4 ± 3.2 [0.5-4.2] | |

TABLE 1-continued

CfDNA level in follicular fluid pools according to the patients' clinical characteristics.

| Variable | Mean | n (total = 100) | Min-Max | SD | FF cfDNA (ng/ul) Mean ± SD [95% CI] | p-value |
|---|---|---|---|---|---|---|
| Antagonist protocol | | | | | | |
| Days of stimulation | 10 | — | 7-13 | 1.2 | | |
| 7-10 | — | 33 | — | — | 1.5 ± 1.6 [1.0-2.1] | 0.11 NS |
| >10 | — | 17 | — | — | 2.2 ± 2.3 [1.0-3.4] | |
| Total dose of gonadotropins (IU/l) | 2475.5 | — | 875-4950 | 982.7 | | |
| <3000 | — | 31 | — | — | 1.6 ± 2.0 [0.9-2.3] | 0.13 NS |
| ≥3000 | — | 19 | — | — | 2.0 ± 1.6 [1.3-2.8] | |
| Hormonal ovarian response at ovulation triggering | | | | | | |
| Peak E2 level (pg/ml) | 1793.2 | — | 341-4768 | 799 | — | — |
| 1000-2000 | — | 56 | — | — | 1.8 ± 2.1 [1.2-2.3] | ref |
| <1000 | — | 12 | — | — | 2.4 ± 3.5 [0.2-4.6] | 0.71 NS |
| >2000 | — | 32 | — | — | 1.4 ± 1.8 [0.8-2.1] | 0.23 NS |
| Progesterone level (ng/ml) | 0.8 | — | 0.1-1.6 | 0.3 | — | — |
| <1 | — | 76 | — | — | 1.7 ± 2.1 [1.2-2.2] | 0.82 NS |
| ≥1 | — | 24 | — | — | 1.8 ± 2.6 [0.7-2.9] | |
| LH level (IU/l) | 2.0 | — | 0.1-6.0 | 1.5 | — | |
| <2 | — | 38 | — | — | 1.9 ± 2.0 [1.3-2.6] | 0.62 NS |
| ≥2 | — | 24 | — | — | 2.3 ± 3.5 [0.8-3.7] | |
| IVF | — | 31 | — | — | 1.7 ± 2.4 [0.8-2.5] | 0.44 NS |
| ICSI | — | 69 | — | — | 1.8 ± 2.2 [1.3-2.3] | |

SD, standard deviation;
BMI, body mass index;
FSH, follicle-stimulating hormone;
LH, luteinizing hormone;
E2, 17β-estradiol;
AMH, anti-Mullerian hormone;
AFC, antral follicle count.
*Total number of patients <100.
P-values: Mann-Whitney test.

In addition, cfDNA was quantified also in FF pools from 17 women with PCOS who were classified according the Rotterdam criteria (Rotterdam ESHRE/ASRM-Sponsored PCOS consensus workshop group. Revised 2003 consensus on diagnostic criteria and long-term health risks related to polycystic ovary syndrome (PCOS). Hum Reprod 2004; 19: 41-7). The clinical characteristics of PCOS patients are reported separately in S1 Table.

Each patient's written informed consent for FF sample collection/analysis was obtained on oocyte retrieval day. This study was approved by the Ethical Committee of the Institute for Regenerative Medicine and Biotherapy and the methods were carried out in accordance with the approved guidelines.

In Vitro Fertilization Protocol and Follicular Fluid Sample Collection

Forty-eight patients received a daily GnRH agonist protocol (Decapeptyl, IpsenPharma) and the others an antagonist protocol. These two protocols included ovarian stimulation by recombinant FSH (r-FSH) (Puregon, MSD, Courbevoie, France). The ovarian response to stimulation was monitored by quantifying serum E2 level and by ultrasound assessment of follicular and endometrial growth. The ovarian stimulation length was 10±1.2 day and the total gonadotropin dose was 2414.7±932.5 IU/l (mean±SD) (Table 2). Ovulation was triggered by a single injection of 250 μg human chorionic gonadotropin (hCG) (Ovitrelle, Merck Serono, Lyon, France), when at least three follicles reached the diameter of 17 mm or more on ultrasound examination.

TABLE 2

CfDNA level in follicular fluid pools according to COS protocols and ovarian response to stimulation.

| Variable | Mean | n (total = 100) | Min-Max | SD | FF cfDNA (ng/μl) Mean ± SD [95% CI] | p-value |
|---|---|---|---|---|---|---|
| Agonist protocol** | — | 48 | — | — | 1.4 ± 2.0 [0.9-2.0] | 0.09 NS |
| Antagonist protocol | — | 50 | — | — | 1.8 ± 1.8 [1.3-2.3] | |
| Ovarian stimulation treatment | | | | | | |
| Days of stimulation | 10 | — | 7-14 | 1.2 | — | — |
| 7-10 | — | 71 | — | — | 1.5 ± 1.9 [1.0-1.9] | 0.008 |
| >10 | — | 29 | — | — | 2.4 ± 2.8 [1.4-3.5] | |

TABLE 2-continued

CfDNA level in follicular fluid pools according to COS protocols and ovarian response to stimulation.

| Variable | Mean | n (total = 100) | Min-Max | SD | FF cfDNA (ng/μl) Mean ± SD [95% CI] | p-value |
|---|---|---|---|---|---|---|
| Total dose of gonadotropins (IU/l) | 2414.7 | — | 875-4950 | 932.5 | — | — |
| <3000 | — | 66 | — | — | 1.5 ± 2.1 [1.0-2.0] | 0.01 |
| ≥3000 | — | 34 | — | — | 2.2 ± 2.3 [1.4-3.0] | |
| Agonist protocol | | | | | | |
| Days of stimulation | 10 | — | 8-14 | 1.1 | | |
| 8-10 | — | 37 | — | — | 1.1 ± 1.1 [0.7-1.4] | 0.05 NS |
| >10 | — | 11 | — | — | 2.7 ± 3.6 [0.3-5.1] | |
| Total dose of gonadotropins (IU/l) | 2324 | — | 900-4200 | 797.8 | | |
| <3000 | — | 34 | — | — | 1.1 ± 1.1 [0.7-1.5] | 0.049 |
| ≥3000 | — | 14 | — | — | 2.4 ± 3.2 [0.5-4.2] | |
| Antagonist protocol | | | | | | |
| Days of stimulation | 10 | — | 7-13 | 1.2 | | |
| 7-10 | — | 33 | — | — | 1.5 ± 1.6 [1.0-2.1] | 0.11 NS |
| >10 | — | 17 | — | — | 2.2 ± 2.3 [1.0-3.4] | |
| Total dose of gonadotropins (IU/l) | 2475.5 | — | 875-4950 | 982.7 | | |
| <3000 | — | 31 | — | — | 1.6 ± 2.0 [0.9-2.3] | 0.13 NS |
| ≥3000 | — | 19 | — | — | 2.0 ± 1.6 [1.3-2.8] | |
| Hormonal ovarian response at ovulation triggering | | | | | | |
| Peak E2 level (pg/ml) | 1793.2 | — | 341-4768 | 799 | — | — |
| 1000-2000 | — | 56 | — | — | 1.8 ± 2.1 [1.2-2.3] | ref |
| <1000 | — | 12 | — | — | 2.4 ± 3.5 [0.2-4.6] | 0.71 NS |
| >2000 | — | 32 | — | — | 1.4 ± 1.8 [0.8-2.1] | 0.23 NS |
| Progesterone level (ng/ml) | 0.8 | — | 0.1-1.6 | 0.3 | — | — |
| <1 | — | 76 | — | — | 1.7 ± 2.1 [1.2-2.2] | 0.82 NS |
| ≥1 | — | 24 | — | — | 1.8 ± 2.6 [0.7-2.9] | |
| LH level (IU/l) | 2.0 | — | 0.1-6.0 | 1.5 | — | — |
| <2 | — | 38 | — | — | 1.9 ± 2.0 [1.3-2.6] | 0.62 NS |
| ≥2 | — | 24 | — | — | 2.3 ± 3.5 [0.8-3.7] | |

E2, 17β-estradiol;
LH, luteinizing hormone;
IVF, in vitro fertilization;
ICSI, intracytoplasmic sperm injection.
**except two mild ovarian stimulations.
P-values: Mann-Whitney test.

Oocyte retrieval was performed by transvaginal ultrasound-guided aspiration 36 h after hCG administration and all follicles were aspirated without flushing. All FF samples collected from the same patient were pooled and cumulus-oocyte complexes were isolated for conventional IVF or ICSI procedures.

Before ICSI, cumulus and coronal cells were removed to assess oocyte maturity rate. On average, 9.5±4.7 oocytes (mean±SD) (S2 Table) were obtained and individually maintained in 30 μl micro-droplets of culture medium (Vitrolife) under oil, at 37° C., in 5% $O_2$, 6% $CO_2$, 89% $N_2$ and in humid atmosphere. Oocytes were considered as normally fertilized if two pronuclei and two polar bodies were observed 18-20 h after microinjection or insemination. Early cleavage was checked at 25 or 27 h after microinjection or insemination, respectively. On day 2 and 3, embryo morphology was evaluated by microscopic observation of morphological criteria, such as number of blastomeres, blastomere regularity and fragmentation rate. Embryo quality was graded from 1 to 4, as described in S3 Table. A top quality embryo (grade 1 and 2) was defined as an embryo with 4-5 or 6-8 regular blastomeres, at day 2 or 3, respectively, and containing less than 20% fragments. At day 3, top quality embryos were selected for transfer or freezing, whereas the others were cultured up to day 5 and frozen by vitrification (Irvine Scientific recommendation), according to their quality, assessed by Gardner scoring (Gardner D K, Lane M, Stevens J, Schlenker T, Schoolcraft W B. Blastocyst score affects implantation and pregnancy outcome: towards a single blastocyst transfer. Fertil Steril 2000; 73: 1155-8). Four weeks after transfer, clinical pregnancy was confirmed by the presence of at least one gestational sac and the visualization of embryonic heart activity on ultrasound examination.

Follicular Fluid Preparation

All FF samples from the same patient were pooled and a volume of 15 ml was centrifuged at 3000 g for 15 min. Supernatants were filtered with 0.45 μm filters to eliminate cell debris and then stored at −80° C. until cfDNA quantification. A total of 117 FF pools were collected for this study.

Cell-Free DNA Extraction and Quantification by ALU-qPCR

FF pools were prepared for cfDNA quantification as previously reported (Umetani N, Kim J, Hiramatsu S, Reber H A, Hines O J, Bilchik A J, et al. Increased integrity of free circulating DNA in sera of patients with colorectal or periampullary cancer: direct quantitative PCR for ALU repeats. Clin Chem 2006; 52: 1062-9). Specifically, 20 µl of each FF pool was digested with 16 µg proteinase K (PK) (Qiagen) in 20 µl of buffer (25 ml/l Tween 20, 50 mmol/l Tris and 1 mmol/l EDTA) at 50° C. for 20 min, followed by PK heat inactivation and insolubilization at 95° C. for 5 min. After centrifugation at 10 000 g for 5 min, supernatants were removed and stored at −80° C. for cfDNA quantification.

CfDNA was quantified by qPCR, using ALU 115 primers (Umetani et al., 2006). Each ALU-qPCR reaction included 1 µl of PK-digested FF pool and a reaction mixture containing 0.25 µM of forward and reverse ALU 115 primers and 5 µL of 2× LightCycler®480 SYBR Green I master mix (Roche Applied Science, Germany). CfDNA concentration in FF pools was determined using a standard curve obtained by successive dilutions of genomic DNA (Umetani et al., 2006). A negative control (without template) was integrated in each qPCR plate and each FF pool was analysed in quadruplicate.

Statistical Analysis

Univariate analysis was performed for each variable. Continuous parametric data are presented as mean±standard deviation (SD) and categorical variables as numbers and percentages. The Mann-Whitney test and Spearman correlations were used to compare cfDNA levels according to quantitative variables, based on the normality of the distribution assessed using the Shapiro-Wilk test. A multivariate analysis was used to model the clinical pregnancy probability. A logistic regression model was fitted in which all variables associated with a p value lower than 0.20 were included in the univariate analysis. Then, a stepwise procedure allowed obtaining the final multivariate model. The ability of FF cfDNA level to predict the clinical pregnancy outcome was determined by constructing the Receiving Operator Curve (ROC) curve and calculating the area under the curve (AUC) with 95% confidence intervals (CI). The sensitivity and specificity for the optimal cut-off were calculated. Statistical tests were performed using the R (version 2.15.2) software. Results were considered significant when $p \leq 0.05$.

Results

Cell-Free DNA Level in FF Pools in Relation to Ovarian Reserve Status and Infertility Length The cfDNA concentration in FF pools of the 17 patients with polycystic ovary syndrome (PCOS) was significantly higher than in FF pools from patients with normal ovarian reserve (n=94) (2.9±3.1 ng/µl versus 1.7±2.3 ng/µl, p=0.049) (FIG. 8). Overall, cfDNA levels were significantly higher in FF pools from patients with ovarian reserve disorders (including LFOR and PCOS) than in FF pools from women with normal ovarian reserve (2.7±2.7 ng/µl versus 1.7±2.3 ng/µl, p=0.03) (FIG. 5A).

Given the specific PCOS clinical profile, we decided to exclude these 17 patients from the subsequent analysis. Moreover, cfDNA concentrations were significantly higher in FF pools from patients with low AFC (<10) than in samples from women with normal AFC (≥10) (2.3±2.6 ng/µl versus 1.5±2.2 ng/µl, respectively, p=0.04) (FIG. 5B, left panel and Table 1). Likewise, FF cfDNA level tended to be higher in women with very low AMH serum concentration at day 3 of the menstrual cycle (≤1 ng/ml) than in those with AMH>1 ng/ml (4.3±5.0 ng/µl versus 1.6±2.0 ng/µl, respectively, p=0.06) (FIG. 5B, right panel and Table 1).

Finally, FF cfDNA levels progressively increased with the infertility length and were significantly higher in patients who had been trying to conceive for more than five years compared to women who tried only for one year (2.9±3.8 ng/l versus 1.1±1.6 ng/µl, p=0.049) (FIG. 5C and Table 1).

Cell-Free DNA Concentration in Follicular Fluid Pools According to COS Protocol and Ovarian Response FF cfDNA level did not vary significantly between women who received GnRH agonists and those treated with antagonists (Table 2). On the other hand, it was significantly higher after long ovarian stimulation (>10 days) than after a short treatment (7-10 days) (2.4±2.8 ng/µl versus 1.5±1.9 ng/µl, p=0.008) (FIG. 6A and Table 2). Likewise, Spearman's correlation analysis showed that FF cfDNA level was significantly and positively correlated with the ovarian stimulation length (r=0.2; p=0.04). Moreover, cfDNA level was significantly higher in FF pools from women who received high total dose of gonadotropins (≥3000 IU/l) than in women treated with lower dose (<3000 IU/l) (2.2±2.3 ng/µl versus 1.5±2.1 ng/µl, p=0.01) (FIG. 6B and Table 2). A similar result was obtained when only patients who received an agonist protocol were considered (2.4±3.2 ng/µl versus 1.1±1.1 ng/µl, p=0.049) (Table 2). In addition, FF pools from patients with a low number of retrieved oocytes (≤6) had a significantly higher cfDNA concentration than those from women with higher number of retrieved oocytes (>6) (2.8±3.5 ng/µl versus 1.4±1.5 ng/µl, p=0.045) (FIG. 6C and S2 Table).

Cell-Free DNA Concentration in Follicular Fluid Pools and Embryo Outcomes

At day 2 post-fertilization, oocyte cohorts that gave rise to a small number of embryos (<2 embryos) were found to be related to FF pools with significantly higher cfDNA level compared to oocyte cohorts from which at least three embryos were obtained (2.5±2.9 ng/µl versus 1.6±2.0 ng/µl, respectively, p=0.03) (FIG. 7A and Table 3). Moreover, 1.8±1.9 and 1.5±1.5 (mean±SD) embryos in each embryo cohort (i.e., embryos obtained for each patient) were considered as top quality (grade 1 and 2) at day 2 and day 3, respectively. At these early cleavage stages, cfDNA concentration was significantly higher in FF pools related to embryo cohorts that included only poor quality embryos (grades 3 and 4), compared to those related to cohorts with at least one top quality embryo (at day 2: 3.0±3.4 ng/µl versus 1.3±1.5 ng/µl, p=0.002; at day 3: 2.5±3.0 ng/µl versus 1.4±1.7 ng/µl, p=0.006, respectively) (FIGS. 7B and 7C, left panels and Table 3). Likewise, Spearman's correlation analysis indicated that there were significant and negative correlations between FF cfDNA concentration and number of top quality embryos (grades 1 and 2) at day 2 and 3 (r=−0.21, p=0.04; r=−0.21; p=0.04, respectively). Moreover, cfDNA level was significantly higher in the FF pools related to embryo cohorts with less than 20% top quality embryos at day 2 and 3 compared to those related to embryo cohorts that included more than 20% top quality embryos (day 2: 2.5±3.1 ng/µl versus 1.3±1.5 ng/µl, p=0.04; day 3: 2.4±3.0 ng/µl versus 1.3±1.4 ng/µl, p=0.02, respectively) (FIGS. 7B and 7C, right panels and Table 3). In addition, the ratio between number of grade 1-2 embryos and the total number of embryos calculated at day 2 and 3 was significantly and negatively correlated with FF cfDNA level (r=−0.27; p=0.01 and r=−0.23; p=0.03, respectively).

Considering each morphological criterion individually at day 3, cfDNA levels tended to be higher in FF pools related to embryos with high fragmentation rate (≥20%) than with low fragmentation rate (<20%) (2.6±3.5 ng/μl versus 1.4±1.3 ng/μl, respectively, p=0.18) (FIG. 7D, left panel and Table 3). Moreover, the ratio between total number of blastomeres and total number of embryos was calculated for each embryo cohort to estimate the global developmental kinetics. At day 3, cfDNA levels were significantly higher in FF pools corresponding to embryo cohorts with a low total blastomere number/total embryo number ratio (<6; delayed development) than in those with normal developmental kinetics (ratio between 6 and 8) (2.8±2.7 ng/μl versus 1.8±2.8 ng/μl, respectively, p=0.02) (FIG. 7D, right panel and Table 3).

TABLE 3

CfDNA levels in follicular fluid pools according to the embryo development outcome at early stages (day 2 and day 3).

| Embryo development outcome | Mean | SD | n | FF cfDNA (ng/μl) Mean ± SD [95% CI] | p-value |
|---|---|---|---|---|---|
| At day 2 | | | | | |
| Total embryo number | 5.3 | 3.7 | — | — | — |
| ≤2 | — | — | 20 | 2.5 ± 2.9 [1.2-3.9] | 0.03 |
| >2 | — | — | 78 | 1.6 ± 2.0 [1.1-2.0] | |
| Grade 1-2 embryos | 1.8 | 1.9 | — | — | — |
| No grade 1-2 | — | — | 26 | 3.0 ± 3.4 [1.7-4.4] | 0.002 |
| ≥1 grade 1-2 | — | — | 65 | 1.3 ± 1.5 [0.9-1.4] | |
| Grade 1-2 embryos/all embryos | 0.3 | 0.28 | — | — | — |
| ratio <0.2 | — | — | 34 | 2.5 ± 3.1 [1.5-3.6] | 0.04 |
| ratio ≥0.2 | — | — | 57 | 1.3 ± 1.5 [0.9-1.7] | |
| At day 3 | | | | | |
| Grade 1-2 embryos | 1.5 | 1.5 | — | — | — |
| No grade 1-2 | — | — | 32 | 2.5 ± 3.0 [1.4-3.6] | 0.006 |
| ≥1 grade 1-2 | — | — | 59 | 1.4 ± 1.7 [1.0-1.8] | |
| Grade 1-2 embryos/all embryos | 0.29 | 0.3 | — | — | — |
| ratio <0.2 | — | — | 39 | 2.4 ± 3.0 [1.4-3.4] | 0.02 |
| ratio ≥0.2 | — | — | 52 | 1.3 ± 1.4 [0.9-1.7] | |
| % fragmentation | 0.19 | 0.11 | — | — | — |
| % fragmentation <20 | — | — | 60 | 1.4 ± 1.3 [1.0-1.7] | 0.18 NS |
| % fragmentation ≥20 | — | — | 31 | 2.6 ± 3.4 [1.3-3.9] | |
| Total blastomere number/total embryo number | — | — | — | — | — |
| ratio = 6-8 | — | — | 45 | 1.8 ± 2.8 [1.0-2.6] | ref |
| ratio <6 | — | — | 11 | 2.8 ± 2.7 [1.0-4.6] | 0.02 |
| ratio >8 | — | — | 35 | 1.4 ± 1.2 [1.0-1.8] | 0.39 NS |

SD, standard deviation.
P-values: Mann-Whitney test.

Predictive Value of Cell-Free DNA in Follicular Fluid Pools for Clinical Pregnancy Outcome After adjustment for the rank of IVF/ICSI attempts and the number of embryos, FF cfDNA level was significantly and independently associated with the clinical pregnancy outcome [Adjusted Odd Ratio: 0.69 [0.5; 0.96], p=0.03] (Table 4). The area under the ROC curve, which quantifies the clinical pregnancy prediction potential of FF ctDNA concentration, was 0.73 [0.66-0.87] with 88% specificity and 60% sensitivity. On the other hand, the number of top quality embryos (grades 1 and 2) did not predict significantly the clinical pregnancy outcome (p=0.42), suggesting that in our population, the predictive value of FF cfDNA level was higher than the number of top quality embryos.

TABLE 4

Multivariate logistic model showing the prediction of clinical pregnancy according to the cfDNA level in follicular fluid pools.

| Parameters | Crude OR [95% CI] | p-value | Adjusted OR [95% CI]* | p-value |
|---|---|---|---|---|
| Probability to obtain a clinical pregnancy | | | | |
| FF cfDNA (ng/μl) | 0.75 [0.55; 1.03] | 0.08 | 0.69 [0.5; 0.96] | 0.03 |
| IVF/ICSI rank number = 1 vs >1 | 2.5 [1.0; 6.27] | 0.05 | 3.6 [1.3; 9.8] | 0.01 |
| Embryo number | 1.15 [1.0; 1.3] | 0.04 | 1.18 [1.01; 1.37] | 0.03 |

OR, odds ratio;
*Adjusted to the rank of IVF/ICSI attempts and the number of embryos.

Discussion

This study demonstrates that cfDNA content in pooled FF samples from the same patient is significantly related to the woman's ovarian reserve status, suggesting that high FF cfDNA level could reflect a poor follicular micro-environment. It also shows that cfDNA levels were significantly higher in FF pools after a long or strong ovarian stimulation than after a short treatment or stimulation with low doses of gonadotropins. Finally, our data indicate that FF cfDNA could be used to predict the clinical pregnancy outcome. Altogether, our results suggest that FF cfDNA quantification could be considered for improving IVF strategy and outcomes.

CfDNA amount was significantly higher in FF pools from women with long infertility length (more than 5 years). Long infertility length is often associated with increased stress in infertile couples (Chiba H, Mori E, Morioka Y, Kashiwakura M, Nadaoka T, Saito H, et al. Stress of female infertility: relations to length of treatment. Gynecol Obstet Invest 1997; 43: 171-7; Lynch C D, Sundaram R, Maisog J M, Sweeney A M, Buck Louis G M. Preconception stress increases the risk of infertility: results from a couple-based prospective cohort study—the LIFE study. Hum Reprod 2014; 29: 1067-75). Interestingly, a recent study reported that blood cfDNA level was higher in patients undergoing IVF and suffering from stress (Czamanski-Cohen J, Sarid O, Cwikel J, Levitas E, Lunenfeld E, Douvdevani A, et al. Decrease in cell free DNA levels following participation in stress reduction techniques among women undergoing infertility treatment. Arch Womens Ment Health 2014; 17: 251-3). Therefore, a long period of stress, caused by the absence of pregnancy, could lead to an increase of apoptotic events in follicular cells and ultimately to higher FF cfDNA levels. Moreover, it has been shown that relaxation techniques may be beneficial during IVF process, to reduce plasma cfDNA levels and to improve pregnancy outcomes (Czamanski-Cohen et al., 2014).

CfDNA levels were significantly higher in FF pools from women suffering from PCOS or more generally with ovarian reserve disorders (PCOS and LFOR). PCOS is the most common endocrinopathy in reproductive age women. A variety of biochemical abnormalities have been described in this syndrome, such as hyperinsulinaemia, leading to high serum insulin levels, and hyperandrogenism via stimulation of ovarian androgen secretion (Goodarzi M O, Dumesic D A, Chazenbalk G, Azziz R. Polycystic ovary syndrome: etiology, pathogenesis and diagnosis. Nat Rev Endocrinol 2011; 7: 219-31). Recently, it was reported that high insulin concentration promotes apoptosis in primary cultured rat ovarian granulosa cells (Ni X R, Sun Z J, Hu G H, Wang R H. High Concentration of Insulin Promotes Apoptosis of Primary Cultured Rat Ovarian Granulosa Cells Via Its Increase in Extracellular HMGB1. Reprod Sci 2015; 22: 271-7). Therefore, high FF cfDNA content in patients with PCOS could be explained by increased apoptosis in granulosa cells due to hyperinsulinaemia. Moreover, we previously reported that cfDNA levels are significantly higher in small follicles compared to large ones (Scalici E, Traver S, Molinari N, Mullet T, Monforte M, Vintejoux E. et al. Cell-free DNA in human follicular fluid as a biomarker of embryo quality. Hum Reprod 2014; 29: 2661-9). PCOS is associated with follicular maturity abnormalities, such as increased number of small pre-antral follicles (Dewailly D, Andersen C Y, Balen A, Broekmans F, Dilaver N, Fanchin R, et al. The physiology and clinical utility of anti-Mullerian hormone in women. Hum Reprod Update 2014; 20: 370-85; Franks S, Stark J, Hardy K. Follicle dynamics and anovulation in polycystic ovary syndrome. Hum Reprod Update 2008; 14: 367-78). These small follicles could contain high cfDNA levels, thus explaining why cfDNA concentration is high in FF pools from patients with PCOS. We also show that FF cfDNA concentration is high in women with poor ovarian reserve (AFC<10 or AMH≤1 ng/ml) (Jayaprakasan K, Campbell B, Hopkisson J, Johnson I, Raine-Fenning N. A prospective, comparative analysis of anti-Müllerian hormone, inhibin-B, and three-dimensional ultrasound determinants of ovarian reserve in the prediction of poor response to controlled ovarian stimulation. Fertil Steril 2010; 93: 855-64; Ficicioglu C, Cenksoy P O, Yildirim G, Kaspar C. Which cut-off value of serum anti-Müllerian hormone level can predict poor ovarian reserve, poor ovarian response to stimulation and in vitro fertilization success? A prospective data analysis. Gynecol Endocrinol 2014; 30: 372-6). As ovarian reserve decline is caused by accelerated apoptosis in ovary (Spencer S J, Cataldo N A, Jaffe R B. Apoptosis in the human female reproductive tract. Obstet Gynecol Surv 1996; 51: 314-23; Seifer D B, Gardiner A C, Ferreira K A, Pelusoi J J. Apoptosis as a function of ovarian reserve in women undergoing in vitro fertilization. Fertil Steril 1996; 66: 593-8; Vital Reyes V S, Téllez Velasco S, Hinojosa Cruz J C, Reyes Fuentes A. [Ovarian apoptosis]. Ginecol Obstet Mex 2001; 69: 101-7), this could lead to an important release of DNA fragments within ovarian follicles. Moreover, in order to optimize their ovarian response, women with poor ovarian reserve receive large gonadotropin doses and at oocyte retrieval day, the practitioner would try to aspirate with more assiduity the smaller follicles to increase number of oocytes. Therefore, in this case follicular fluids from smaller follicles would become proportionally more represented in the pool than in normal responders with a synchronized cohort of larger follicles. These observations suggest that cfDNA content in antral follicles could depend on (i) the basal ovarian status (increased cfDNA in the case of ovarian dysfunction) and/or on (ii) the follicular maturity after recruitment by COS protocols.

Indeed, FF cfDNA level was significantly higher after a long COS protocol (>10 days) or after administration of high doses of gonadotropins (≥3000 IU/l). Moreover, the ovarian reserve status strongly influences the ovarian response to COS protocols (Dewailly D, Andersen C Y, Balen A, Broekmans F, Dilaver N, Fanchin R, et al. The physiology and clinical utility of anti-Mullerian hormone in women. Hum Reprod Update 2014; 20: 370-85; Younis J S, Skournik A, Radin O, Haddad S, Bar-Ami S, Ben-Ami M. Poor oocyte retrieval is a manifestation of low ovarian reserve. Fertil Steril 2005; 83: 504-7; La Marca A, Sunkara S K. Individualization of controlled ovarian stimulation in IVF using ovarian reserve markers: from theory to practice. Hum Reprod Update 2014; 20: 124-40). For instance, long or strong ovarian stimulation is currently recommended for women at risk of poor ovarian response (Ficicioglu C, Cenksoy P O, Yildirim G, Kaspar C. Which cut-off value of serum anti-Müllerian hormone level can predict poor ovarian reserve, poor ovarian response to stimulation and in vitro fertilization success? A prospective data analysis. Gynecol Endocrinol 2014; 30: 372-6; Lan V T, Linh N K, Tuong H M, Wong P C, Howles C M. Anti-Müllerian hormone versus antral follicle count for defining the starting dose of FSH. Reprod Biomed Online 2013; 27: 390-9). Accordingly, patients who received long stimulation or high gonadotropin dose partially overlaps with patients with high intra-follicular cfDNA levels related to low ovarian reserve. Moreover, high FF cfDNA level after long or strong stimulation could represent a true effect of COS protocols, with potential harmful consequences on IVF/ICSI outcomes. For instance, strong supra-physiological gonadotropin doses could induce apoptosis of follicular cells (Liu S, Feng H L, Marchesi D, Chen Z J, Hershlag A. Dose-dependent effects of gonadotropin on oocyte developmental competence and apoptosis. Reprod Fertil Dev 2011; 23: 990-6), suggesting the necessity to specifically tailor stimulation treatments to each patient's profile. Conversely, FF cfDNA content did not differ according to the type of COS protocols (agonist versus antagonist). In agreement, similar apoptosis levels were detected in granulosa cells exposed to agonist or antagonist treatments (Lavorato H L, Oliveira J B, Petersen C G, Vagnini L, Mauri A L, Cavagna M, et al. GnRH agonist versus GnRH antagonist in IVF/ICSI cycles with recombinant LH supplementation: DNA fragmentation and apoptosis in granulosa cells. Eur J Obstet Gynecol Reprod Biol 2012; 165: 61-5).

FF cfDNA concentration was also significantly higher in patients from whom few oocytes were retrieved (≤6) (Broekmans F J, Verweij P J, Eijkemans M J, Mannaerts B M, Witjes H. Prognostic models for high and low ovarian responses in controlled ovarian stimulation using a GnRH antagonist protocol. Hum Reprod 2014; 29: 1688-97) or few embryos obtained (≤2) This observation confirms that high FF cfDNA level is significantly associated with poor ovarian response to COS protocols. Moreover, it suggests that FF cfDNA level is related to both retrieved oocyte quantity and quality, two key features for embryo production. Indeed, it is largely recognized that the follicular environment influences strongly the oocyte developmental competence (Mendoza C, Ruiz-Requena E, Ortega E, Cremades N, Martinez F, Bernabeu R, et al. Follicular fluid markers of oocyte developmental potential. Hum Reprod 2002; 17: 1017-22; Baka S, Malamitsi-Puchner A. Novel follicular fluid factors influencing oocyte developmental potential in IVF: a review. Reprod Biomed Online 2006; 12: 500-6; Revelli A, Delle Piane L, Casano S, Molinari E, Massobrio M, Rinaudo P. Follicular fluid content and oocyte quality: from single biochemical markers to metabolomics. Reprod Biol Endocrinol 2009; 7: 40; Carpintero N L, Suarez O A, Mangas C C, Varea C G, Rioja R G. Follicular steroid hormones as markers of oocyte quality and oocyte development potential. J Hum Reprod Sci 2014; 7: 187-93). For this reason, FF cfDNA could represent a new promising biomarker of follicular microenvironment quality. A poor follicular microenvironment, with high cfDNA levels could affect oocyte developmental competence and embryo development, thus leading to IVF failure. As we found that strong or long ovarian stimulation leads to high FF cfDNA level, it could be recommended to adapt the stimulation length and gonadotropin dose to each patient to limit FF cfDNA production. Indeed, the preservation of the follicular microenvironment is primordial to obtain competent oocytes and thus competent embryos.

This study confirms our previous observation (Scalici et al., 2014) that cfDNA levels in FF samples are significantly correlated with embryo quality during early development, when embryos rely on the oocyte maternal reserve (on day 2 and 3). Indeed, cfDNA levels were significantly higher in FF pools related to oocyte cohorts that gave only poor quality embryos, embryos with high fragmentation rate (≥20%) or developmentally delayed embryos (total blastomere number/total embryo number ratio<6). These poor quality embryos came from oocyte cohorts surrounded by FF containing high cfDNA levels, suggesting a negative effect of a cfDNA-rich follicular environment on embryo quality (Scalici et al., 2014). In agreement with these results, high mitochondrial DNA level in embryo culture medium was also significantly associated with high fragmentation rate at early embryo cleavages (Stigliani S, Anserini P, Venturini P L, Scaruffi P. Mitochondrial DNA content in embryo culture medium is significantly associated with human embryo fragmentation. Hum Reprod 2013; 28: 2652-60).

Finally, FF CfDNA level in a multivariate model predicted independently and significantly the clinical pregnancy outcome with high specificity (88%). FF cfDNA level predictive potential was higher than that of the number of top quality embryos (based on morphological criteria). Therefore, this predictive model could be used as a supplemental tool for determining the chance of IVF success. Recently, a significant association between the mitochondrial DNA/genomic DNA ratio in embryo culture medium and implantation outcome was reported (Stigliani S, Persico L, Lagazio C, Anserini P, Venturini P L, Scaruffi P. Mitochondrial DNA in Day 3 embryo culture medium is a novel, non-invasive biomarker of blastocyst potential and implantation outcome. Mol Hum Reprod 2014; 20: 1238-46). Moreover, Czamanski-Cohen et al. found higher cfDNA level in serum samples from patients with low pregnancy rates after IVF, suggesting that circulating DNA fragments from apoptotic maternal cells could have a damaging effect. As there is fluid components' movement between follicles and vasculature (Rodgers R J, Irving-Rodgers H F. Formation of the ovarian follicular antrum and follicular fluid. Biol Reprod 2010; 82: 1021-9), these fragments could come from massive apoptotic events that occur in the ovaries and that contribute to increasing cfDNA level in FF samples.

In addition, cfDNA quantification in FF pools, fast and easy to perform, could provide an overall picture of the follicular micro-environment quality, influencing IVF outcomes. Therefore, this quantification could be associated with the morphology-based method in order to improve embryo selection for replacement or freezing and consequently the chance of IVF success. This biomarker might constitute a supplemental tool for improving female infertility management and developing a personalized care program.

S1 TABLE

Clinical characteristics and ovarian response to stimulation of patients with polycystic ovary syndrome (PCOS) (n = 17).

| Variable | Mean | n (total = 17) | SD |
|---|---|---|---|
| Age (years) | 33.5 | — | 4.2 |
| <37 years | — | 14 | — |
| ≥37 years | — | 3 | — |
| BMI (kg/m$^2$) | 26.7 | — | 5.9 |
| 18.5 ≤ BMI < 25 | — | 6 | — |
| BMI < 18.5 | — | 1 | — |
| 25 ≤ BMI < 30 | — | 5 | — |
| BMI ≥ 30 | — | 5 | — |
| Infertility lenght (years) | 3.8 | — | 1.3 |
| 1 | — | 1 | — |
| 2-4 | — | 12 | — |
| ≥5 | — | 4 | — |
| Primary infertility | — | 6 | — |
| Secondary infertility | — | 11 | — |
| IVF/ICSI cycle number | 1.9 | — | 1.2 |
| 1 | — | 7 | — |
| >1 | — | 10 | — |
| Baseline evaluation | | | |
| FSH (IU/l) | 5.8 | — | 1.8 |
| LH (IU/l) | 6.9 | — | 3.5 |
| E2 (pg/ml) | 36.3 | — | 15.1 |
| AMH (ng/ml) | 7.4 | — | 3.5 |
| AFC | 26 | — | 11.5 |
| Agonist protocol | — | 13 | — |
| Antagonist protocol | — | 4 | — |
| Days of stimulation | 10 | — | 1.7 |
| Total dose of gonadotropins (IU/l) | 1917.2 | — | 751.7 |
| Hormonal ovarian response at ovulation triggering | | | |
| Peak E2 level (pg/ml) | 2068.9 | — | 847.2 |
| Progesterone level (ng/ml) | 0.7 | — | 0.4 |
| LH level (IU/l) | 2.4 | — | 1.8 |

SD, standard deviation;
BMI, body mass index;
FSH, follicle-stimulating hormone;
LH, luteinizing hormone;
E2, 17β-estradiol;
AMH, anti-Müllerian hormone;
AFC, antral follicle count;
IVF, in vitro fertilization;
ICSI, intracytoplasmic sperm injection.

S2 Table: CfDNA level in follicular fluid pools according to oocyte retrieval, fertilization and early cleavage outcomes.

| Oocyte retrieval, fertilization and early cleavage outcomes | Mean | SD | n | FF cfDNA (ng/l) Mean ± SD [95% CI] | p-value |
|---|---|---|---|---|---|
| Oocytes | 9.5 | 4.7 | — | — | — |
| ≤6 | — | — | 25 | 2.8 ± 3.5 [1.4-4.2] | 0.045 |
| >6 | — | — | 75 | 1.4 ± 1.5 [1.0-1.7] | |
| Empty zona pellucida | 0.4 | 0.8 | — | — | |
| No Empty zona pellucida | — | — | 87 | 1.5 ± 1.8 [1.1-1.9] | 0.3 NS |
| ≥1 Empty zona pellucida | — | — | 24 | 2.4 ± 3.2 [1.2-3.7] | |

S2 Table: CfDNA level in follicular fluid pools according to oocyte retrieval, fertilization and early cleavage outcomes.

| Oocyte retrieval, fertilization and early cleavage outcomes | Mean | SD | n | FF cfDNA (ng/l) Mean ± SD [95% Cl] | p-value |
|---|---|---|---|---|---|
| Mature oocytes (MII) | 7.2 | 4.1 | — | — | — |
| <5 | — | — | 19 | 2.4 ± 3.1 [1.0-3.9] | 0.25 NS |
| ≥5 | — | — | 50 | 1.5 ± 1.6 [1.1-2.0] | |
| Mature oocytes/oocytes | 0.76 | 0.21 | — | — | — |
| ratio < 0.75 | — | — | 26 | 1.5 ± 1.5 [0.8-2.1] | 0.45 NS |
| ratio ≥ 0.75 | — | — | 43 | 2.0 ± 2.4 [1.2-2.7] | |
| Immature oocytes (GV, MI) | 1.8 | 1.9 | — | — | — |
| <3 | — | — | 67 | 1.9 ± 2.5 [1.3-2.5] | 0.97 NS |
| ≥3 | — | — | 33 | 1.4 ± 1.4 [1.0-1.9] | |
| Immature oocytes/oocytes | 0.18 | 0.18 | — | — | — |
| ratio < 0.25 | — | — | 70 | 1.9 ± 2.5 [1.3-2.5] | 0.26 NS |
| ratio ≥ 0.25 | — | — | 30 | 1.3 ± 1.5 [0.8-1.9] | |
| Atretic oocytes | 0.3 | 0.8 | — | — | — |
| No atretic oocyte | — | — | 85 | 1.7 ± 2.3 [1.2-2.3] | 0.44 NS |
| ≥1 atretic oocyte | — | — | 15 | 1.7 ± 1.3 [1.0-2.4] | |
| Atretic oocytes/oocytes | 0.02 | 0.07 | — | — | — |
| ratio ≤ 0.1 | — | — | 88 | 1.7 ± 2.3 [1.2-2.2] | 0.19 NS |
| ratio > 0.1 | — | — | 12 | 1.9 ± 1.3 [1.0-2.7] | |
| Fertilization | | | | | |
| % IVF/ICSI fertilization | 0.65 | 0.3 | — | — | — |
| <0.65 | — | — | 20 | 1.9 ± 1.7 [1.2-2.7] | 0.27 NS |
| ≥0.65 | — | — | 79 | 1.7 ± 2.4 [1.2-2.2] | |
| At 25-27 hours after fertilization | | | | | |
| Early cleavage | 1.8 | 2.6 | — | — | — |
| No | — | — | 36 | 1.9 ± 2.7 [1.0-2.9] | 0.72 NS |
| ≥1 | — | — | 55 | 1.7 ± 2.0 [1.1-2.2] | |
| Early cleavage/2PN | 0.41 | 0.88 | — | — | — |
| ratio ≤ 0.5 | — | — | 68 | 2.0 ± 2.6 [1.4-2.6] | 0.18 NS |
| ratio > 0.5 | — | — | 21 | 1.0 ± 0.8 [0.7-1.4] | |
| % fragmentation | 0.07 | 0.09 | — | — | — |
| <10% | — | — | 31 | 1.3 ± 1.3 [0.9-1.8] | 0.25 NS |
| ≥10% | — | — | 24 | 2.1 ± 2.6 [1.0-3.2] | |

SD, standard deviation;
MII, oocyte blocked in meiotic metaphase II;
GV, germinal vesicle;
MI, oocyte blocked in meiotic metaphase I;
IVF, in vitro fertilization;
ICSI, intracytoplasmic sperm injection.
P-values: Mann-Whitney test.

S3 TABLE

Embryo quality classification at day 2 and day 3 post-fertilization.

| Morphological criteria | grade | | | | |
|---|---|---|---|---|---|
| Number of blastomeres | 1 | 2 | 3 | 4 | |
| Day 2 | 4-5 | 4-5 | 4-5 | <4 or >5 | — |
| Day 3 | 6-8 | 6-8 | 6-8 | <6 or >8 | — |
| Blastomere regularity | Regular | Regular | Regular or irregular | Regular or irregular | Regular or irregular |
| Fragmentation rate (%) | ≤10 | 10-19 | 20-40 | <40 | >40 |

Embryo quality was graded from 1 to 4 (1-2 for top quality embryos; 3-4 for poor quality embryos), based on the following morphological criteria: number of blastomeres, blastomere regularity and fragmentation rate Example 3

Materials and Methods

Patients

This prospective study included 131 women who underwent conventional IVF (n=32) or ICSI (n=99) at the ART-PGD Department of the University Hospital of Montpellier, France. Their mean age was 34.7±4.5 years (mean±SD; range: 19 to 43 years) and the body mass index (BMI) was 23.4±4.5 kg/m$^2$ (mean±SD; range: 17 and 37.5 kg/m$^2$) (Table 7). The infertility length was 3.6±1.5 years (mean±SD) and infertility was primary in 78 couples and secondary in the other 53. Male, female and mixed factors were detected in 31.3%, 37.4% and 25.2% of cases, respectively, while infertility was unexplained in 6.1% of couples. This was the first IVF or ICSI attempt for 38.9% of them, while 61.1% had already undergone at least one cycle (mean number of cycles±SD: 2.1±1.3). Among the 131 women, 91 had a normal ovarian reserve and 10 had LFOR, based on the serum AMH level and AFC, evaluated at day 3 of the menstrual cycle. The other 30 women had PCOS, according to the Rotterdam criteria (Rotterdam, 2004). Basal follicle-stimulating hormone (FSH), luteinizing hormone (LH) and 17βestradiol (E2) serum levels were also measured in each patient at day 3 of the menstrual cycle. The clinical characteristics of all women and in the three groups (normal ovarian reserve, PCOS and LFOR) are detailed in Table 7. Patients were informed about FF sample collection/analysis and they gave their written informed consent on oocyte retrieval day. The local Institutional Review Board approved this investigation.

IVF Procedure

A gonadotropin-releasing hormone (GnRH) agonist (Decapetyl, IpsenPharma) was administered daily to 63 women and an antagonist protocol was used in 64. The remaining four patients received a mild treatment and were thus excluded from the analysis concerning the treatment effect on miRNA expression. These two protocols included COS with two types of gonadotropins: recombinant FSH (r-FSH) (Puregon, MSD, Courbevoie, France or GonalF, Merck Serrono, Lyon, France), or highly purified human menopausal gonadotropin (hMG) (Menopur, Ferring, Gentilly, France). COS duration was 10.5±1.4 days and the total gonadotropin dose was 2501±673 IU/l (mean±SD) (Table 7). The ovarian response to stimulation was monitored by measuring the serum E2 concentration and by ultrasound assessment of follicular and endometrial growth. Ovulation was triggered with an injection of 250 µg human chorionic gonadotropin (hCG) (Ovitrelle, Merck Serono, Lyon, France) when at least three follicles reached the diameter of 17 mm or more on ultrasound examination. At ovulation triggering day, the hormonal ovarian response was also evaluated by quantifying serum E2, LH and progesterone levels (Table 7).

Oocytes were retrieved by transvaginal ultrasound-guided aspiration 36 h after hCG injection. For each patient, all follicles were aspirated without flushing, cumulus-oocyte complexes were isolated for conventional IVF or ICSI and all FF samples were collected.

Before intracytoplasmic sperm microinjection, the oocyte maturity rate (77%) was assessed after denudation. On average, 7.6±4.5 oocytes (mean±SD) and 6±3.7 mature oocytes (MII) (mean±SD) were collected per patient (Table 8). Oocytes were cultured individually in 30 µl microdroplets of culture medium (Vitrolife) under oil at 37° C. in 5% $O_2$, 6% $CO_2$ and 89% $N_2$, in humid atmosphere. The presence of two pronuclei and two polar bodies, 18-20 h after microinjection or insemination confirmed that the cultured oocytes were normally fertilized (overall fertilization rate=64%). For each patient, 4.1±3.3 embryos were obtained from the fertilized oocytes at day 2. Among these embryos, 1.3±1.4 were cleaved early at 25 or 27 h after microinjection or insemination, respectively. On day 3, embryo quality was assessed based on morphological criteria (blastomere number, blastomere regularity and fragmentation rate). On average, 1.2±1.6 embryos/patient (mean±SD) were considered as top quality because they contained 6-8 regular blastomeres and less than 20% fragments. One or two top quality embryos were transferred in utero at day 3, whereas the others were further cultured up to day 5. Blastocysts were classified according to the scoring system developed by Gardner (Gardner et al., 2000). At day 5, only expanded blastocysts (classified as grade 4 or 5) with inner cell mass and trophectoderm scored as A or B were vitrified using a closed system, following the procedure recommended by Irvine Scientific. Four weeks after embryo transfer, clinical pregnancy was confirmed by the observation of at least one gestational sac and of embryonic heart activity on ultrasound examination. The IVF/ICSI outcomes of all women and in the three groups (normal ovarian reserve, PCOS and LFOR) are reported in Table 8.

FF Sample Preparation

At oocyte retrieval day, all FF samples of a patient were collected and pooled (n=131 pools). A volume of 15 ml from each pool was centrifuged at 3000 g for 15 min. Then, supernatants were removed, filtered through 0.45 µm filters to eliminate cell debris and stored at −80° C.

MiRNA Extraction

The QIAamp® Circulating Nucleic Acid kit (ref. 55114; Qiagen) was used for isolation and purification of circulating miRNAs from 3 ml of each FF pool according to the manufacturer's protocol. Briefly, 3 ml of FF pool, 400 µl of Qiagen Proteinase K and 4.2 ml of buffer ACL were mixed by pulse vortexing and incubated at 60° C. for 30 min. After incubation, 9 ml of buffer ACB was added to the lysate and mixed by pulse vortexing. The mixture was then transferred in a QIAamp Mini column by vacuum pressure to adsorb the miRNAs onto a small silica membrane. Next, each membrane was washed in three steps to remove residual contaminants. Highly pure circulating microRNAs were eluted within 40 µl of buffer AVE.

FF miRNA Expression Analysis by RT-qPCR

Complementary DNA (cDNA) was generated using the TaqMan MicroRNA reverse transcription kit and miRNA-specific stem-loop primers for let-7b, miR-29a, miR-30a, miR-140, miR-191 and miR-320a (ref 4427975, Life Technologies). The 15 µl reaction mix contained 5 µl of FF pool, 0.15 µl of 100 mM dNTP, 1.5 µl of 10×RT Buffer, 1 µl of MultiScribe RT enzyme (50 U/µl), 0.19 µl of RNase inhibitor (20 U/µl), 4.16 µl of nuclease-free water and 3 µl of Taqman RT primer. Reverse transcription was carried out at 16° C. for 30 min and then at 42° C. for 30 min, followed by an inactivated step at 85° C. for 5 min and an hold step at 4° C. Quantitative PCR was performed in duplicate for each sample using LightCycler 480® (Roche Applied Science, Germany); a negative control (water) was added for each FF pool. PCR reactions were carried out in a total volume of 10 µl, consisting of 3 µl of cDNA, 5 µl of Taqman Universal PCR MasterMix (Applied Biosystems) and 2 µl of primer (Life Technologies). The mixture was incubated in a 384-well plate, at 95° C. for 10 min, followed by 50 cycles at 95° C. for 15 s and 60° C. for 1 min. Moreover, miR-16 was used as an internal control, due to its stability in body fluids (Kroh et al., 2010; Song et al., 2012), to normalize the miRNA expression levels. The relative expression of the six miRNAs (let-7b, miR-29a, miR-30a, miR-140, miR-191 and miR-320a) in each FF pool was calculated relative to that of miR-16 by using the equation $2^{-Ct}$, in which ΔCt was determined by the formula: Ct target miRNA—Ct miR-16.

These six miRNAs were chosen because previous studies reported that they are expressed in FF (Sang et al., 2013; Feng et al., 2015).

Pathway Analysis

Pathway Studio® (Elsevier) was used to identify the biological processes in which the miRNAs detected in FF pools are involved in the reproductive system. Key pathways included follicular development, cell proliferation, apoptosis, steroidogenesis, meiosis and embryo implantation. The interactions between some miRNAs and steroid hormones were also integrated in this pathway analysis.

Statistical Analysis

Univariate analysis was performed for each variable. Continuous parametric data are presented as the mean±standard deviation (SD) and categorical variables with numbers and percentages. The Mann-Whitney test, Student's t test, Anova or Kruskal Wallis test were used for quantitative variables, based on the normality of the distribution, assessed using the Shapiro-Wilk test. Multivariate analysis was used to investigate differential miRNA expression related to ovarian reserve disorders (PCOS and LFOR). A logistic regression model was fitted in which all variables associated with a p value lower than 0.20 were included in the univariate analysis. Then, a stepwise procedure allowed obtaining the final multivariate model. The ability of FF miRNA levels to predict ovarian reserve disorders (PCOS and LFOR), blastocyst and clinical pregnancy outcomes was assessed by constructing the Receiver Operating Characteristic (ROC) curves and calculating the area under the ROC curve (AUC) with 95% confidence interval (CI). The sensitivity and specificity of the optimal cut-off were calculated. Statistical tests were performed using the R software (version 2.15.2). Results were considered significant when p≤0.05.

Results

MiRNA Differential Expression in FF Samples from Women with PCOS Compared to Women with Normal Ovarian Reserve Comparison of the expression profiles showed that miR-30a was significantly up-regulated (p=0.006), while miR-140 and let-7b were significantly down-regulated (p=0.01 for both) in FF pools from patients with PCOS compared to women with normal ovarian reserve (FIG. 9). Moreover, these three miRNAs were significantly and independently associated with PCOS in multivariate analysis (adjusted odds ratio, AOR: 5.0 [1.86; 13.68], p=0.001; 0.52 [0.29; 0.94], p=0.03; 1.0 [0.99; 1.0], p=0.02, respectively) (Table 5). Then, the sensitivity and specificity of the relationship between FF miR-30a, miR-140 and let-7b differential expression and PCOS were determined using the ROC curve analysis and by calculating the AUC. The AUC values for the individual performance of FF miR-30a, FF miR-140 and FF let-7b expression profiles in PCOS discrimination were 0.67 (0.57-0.76), 0.67 (0.57-0.76) and 0.67 (0.57-0.76) (p=0.02, p=0.007, p=0.003), respectively (Table 6). By combining the three miRNAs in multivariate analysis, the AUC value increased to 0.83 (0.73-0.92) (p<0.0001) (Table 6). Moreover, the sensitivity and the specificity of FF miR-30a, FF miR-140 and FF let-7b were 57.7%, 57.7% and 53.9% and 85.1%, 81.1% and 75.7%, respectively (Table 6). The combination of these three miRNAs increased the sensitivity of the prediction to 70% with a specificity of 83.8%. These results indicate that the combination of miR-30a, miR-140 and let-7b, which are differentially expressed in FF samples from patients with PCOS compared to women with normal ovarian reserve, gives the largest AUC value with high sensitivity and specificity, and suggest that these three miRNAs represent new potential PCOS biomarkers.

MiRNA Differential Expression in FF Samples from Women with LFOR Compared to Women with Normal Ovarian Reserve Comparison of mRNA expression in FF pools from women with LFOR and with normal ovarian reserve showed that miR30a and miR-191 were up-regulated (p=0.01 for both) in the LFOR group compared to patients with normal ovarian reserve (FIGS. 9A and 10D). However, a significant and positive association was found only between FF miR-191 expression and LFOR, using a logistic regression model [Crude odds ratio, COR: 1.4 [1.03; 1.93], p=0.03] (Table 5). The AUC values of the individual discrimination power of FF miR-30a and miR-191 for LFOR prediction were 0.79 (0.68-0.87) and 0.77 (0.67-0.86) (p<0.0001, p=0.002), respectively (Table 6). The combination of these two miRNAs improved LFOR detection and the corresponding AUC reached 0.84 (0.67-0.86) with a p-value<0.0001 (Table 6). In addition, this combination was very sensitive (85.9%) and specific (71.4%) (Table 6), suggesting that, together, miR-30a and miR-191 are new promising biomarkers for the identification of women with LFOR.

Differential Expression of FF miRNAs According to the Gonadotropin Treatment and Ovarian Response.

The expression of the six miRNAs was comparable in FF pools from women who received agonist or antagonist protocols. Conversely, FF expression of miR-29a and miR-140 varied significantly according to the gonadotropin treatment. Specifically, miR-29a expression was significantly decreased and miR-140 expression significantly increased in FF pools from women treated with hMG compared with patients who were stimulated with r-FSH (p=0.03; p=0.02, respectively) (FIG. 12A). Moreover, whatever the type of gonadotropin, miR-140 was significantly up-regulated in FF pools from women who received higher total doses of gonadotropins (≥3000 IU/l) compared to those treated with lower doses (<3000 IU/l) (p=0.03) (FIG. 12B). Likewise, Spearman's correlation analysis showed that FF miR-140 level was significantly and positively associated with the total dose of gonadotropins (r=0.21; p=0.02).

At oocyte retrieval day, miR-320a level in FF pools was significantly and positively correlated with the number of mature oocytes (MII) (r=0.24; p=0.02). FF pools from women with a low number of mature oocytes (≤2) contained significant lower FF miR-320 levels than those related to a number of mature oocytes higher than 2 (p=0.04) (FIG. 12C).

FF let-7b Expression and Blastocyst Development

By considering only the group of women with normal ovarian reserve (n=91), we found a significant and negative correlation between FF let-7b expression level and blastulation rate (r=−0.33, p=0.003) Indeed, low FF let-7b expression was significantly associated with the probability to obtain a blastocyst [COR=1.0 [0.99; 1.0], p=0.04]. The AUC value of FF let-7b potential to predict blastocyst development, was 0.66 (0.55-0.76) with 77.2% sensitivity and 59.1% specificity (p=0.02; at cut-off value≤273.2). Likewise, FF let-7b levels were also correlated significantly and negatively with the expanded blastocyst rate in women with normal ovarian reserve (r=−0.28. p=009). The probability to obtain an expanded blastocyst was significantly associated with intra-follicular expression of let-7b [COR=1.0 [0.99; 1.0], p=0.02]. In addition, the AUC value that defined the performance of FF let-7b in predicting the formation of expanded blastocysts was 0.67 (0.54-0.79), with 70% sensitivity and 64.3% specificity (p=0.02; at cut-off value≤247.9).

FF miR-29a Predictive Value for Clinical Pregnancy Outcome

In the group with normal ovarian reserve (n=91), FF miR-29a expression predicted significantly the clinical pregnancy outcome [COR=2.08 [1.0; 4.3], p=0.049]. Moreover, the ROC curve analysis indicated that the performance of FF miR-29a for clinical pregnancy prediction reached 0.68 (0.55-0.79) with a sensitivity of 83.3%, but a low specificity (53.5%) (p=0.01; cut-off value >0.32). In addition, comparison of the discrimination power of FF miR-29a expression and of the top quality embryo percentage for clinical pregnancy prediction showed that the AUC value related to FF miR-29a expression was higher than that for the top quality embryo percentage (AUC=0.59 [0.46-0.72]; p=0.27).

Biological Functions of the Candidate miRNAs in the Reproductive System

MiR-29a, miR-320a, let-7b and miR-30a, identified as differentially expressed in FF pools, are involved in several pathways of the reproductive system. Pathway Studio® was used to generate a schematic view of the different regulatory roles of these miRNAs in reproductive processes, such as follicular growth, apoptosis, steroidogenesis, meiosis and embryo implantation (FIG. 15). The schematic also integrated the interactions with steroid hormones (estrogen and progesterone). The potential functions of these miRNAs, their localization in the ovarian follicle and their primary targets are summarized in Table 9.

Discussion

This study investigated the expression profiles of six circulating miRNAs (let-7b, miR-29a, miR-30a, miR-140, miR-191 and miR-320a) in FF pools from patients undergoing IVF/ICSI procedures and found that they are differentially expressed according to the women's ovarian reserve status, gonadotropin treatments and/or IVF outcomes (FIG. 4). Our data suggest that these circulating miRNAs might represent new powerful tools to monitor IVF, by identifying efficiently women with ovarian reserve disorders (PCOS or LFOR) and by predicting IVF outcomes, such as blastocyst development or clinical pregnancy outcomes.

We demonstrate, for the first time, that the expression of let-7b and miR-140 is significantly decreased whereas miR-30a is up-regulated in FF samples from patients with PCOS. Moreover, the combination of these three miRNAs is significantly associated with PCOS, with high specificity and sensitivity. Therefore, they could constitute new specific biomarkers to easily and efficiently identify women with PCOS. Previous studies reported that let-7b is expressed in granulosa and cumulus cells in mammalian and also human ovaries (Yao et al., 2009; Miles et al., 2012; Zhang et al., 2013; Kim et al., 2013; Assou et al., 2013; Cao et al., 2015). PCOS is characterized by follicular development abnormalities, suggesting that the normal "dialogue" between oocyte and granulosa cells in early growing follicles might be altered (Franks et al., 2008). Accordingly, the significant decrease of FF let-7b expression observed in patients with PCOS might reflect this abnormal folliculogenesis. Indeed, it has been reported that let-7b could play a specific role in ovarian follicular development (Yao et al., 2009; Zhang et al., 2013; Cao et al., 2015). Specifically, let-7b regulates the TGF-β signaling pathway in goat ovary by targeting the activin receptor I and Smad2/3 genes (Zhang et al., 2013). TGF-β dysregulation contributes to reproductive abnormalities in PCOS, such as follicle development perturbation (Raja-Khan et al., 2014). Consequently, let-7b down-regulation in ovarian follicles could lead to TGF-β signaling pathway deregulation and ultimately contribute to PCOS development. Abnormal estrogen receptor (ER) expression could also contribute to poor follicular development and ovulatory failure in PCOS (Jakimiuk et al., 2002). MiR-140 plays a role as tumor suppressor and is down-regulated in breast cancer via ERα signaling (Zhang et al., 2012). These findings suggest that the modifications of ERα expression observed in PCOS might influence negatively miR-140 expression in ovarian follicles. Finally, it has been demonstrated that miR-30a overexpression in cultured human granulosa cells promotes BCL2A1, IER3 and cyclin D2 expression by repressing FOXL-2 (Wang et al., 2015). FOXL-2 encodes a forkhead transcription factor that is essential for ovarian development (Crisponi et al., 2001). FOXL-2 conditional knockout in mouse results in sex-reversed follicles with characteristics of cystic follicles, including elevated androgen production by theca cells and morphological transformation of granulosa cells, like in PCOS (Uhlenhaut et al., 2009; Murphy, 2010). Moreover, androgen-induced hirsutism, described in patients with PCOS, is also observed in women carrying FOXL-2 mutations (Meduri et al., 2010). Based on these observations, we hypothesize that miR-30 overexpression in FF pools from women with PCOS might lead to FOXL-2 inhibition/down-regulation in ovarian follicles, thus promoting PCOS symptom development. Differently from two previous study (Sang et al., 2013; Yin et al., 2014), FF miR-320a expression was not affected in our group of women with PCOS. However, miR-320a expression level was significantly lower in FF pools from women with less than two mature oocytes (≤2) compared with women with more than two mature oocytes. In the mouse, miR-320a knockdown in oocytes decreased significantly the proportion of mature oocytes that developed into embryos (Feng et al., 2015). Taken together, these data suggest that miR-320a is indicative of mature oocyte quantity and quality and that its intra-follicular expression could be modulated by the ovarian response quality of patients undergoing IVF.

We then found that the expression of miR-30a and miR-191 is significantly higher in FF pools from women with LFOR compared to women with normal reserve status. Moreover, the combination of these two circulating miRNAs discriminated significantly women with LFOR, with high sensitivity and specificity. Therefore, they could represent new specific biomarkers for the identification of women with LFOR. We already discussed the link between miR-30a overexpression and FOXL-2 down-regulation in granulosa cells (Wang et al., 2015). Moreover, FOXL-2 expression reduction/ablation or FOXL-2 mutations affect significantly follicle development (Murphy, 2010). Indeed, in mice, FOXL-2 disruption causes ovarian failure by blocking follicle development (Uda et al., 2004). Likewise, FOXL-2 mutations result in POF and infertility in women by depletion of the follicle reserve, which could be due to disruption of the follicle assembly or to elevated recruitment of primordial follicles (Murphy, 2010). Therefore, we hypothesize that miR-30 over-expression in ovarian follicles may cause FOXL-2 gene repression in follicular cells and consequently lead to decreased ovarian reserve. Moreover, miR-191 is an ER target in breast cancer (Nagpal et al., 2013) and a recent study reported that some miRNAs related to breast cancer risk are also associated with ovarian insufficiency risk (Rah et al., 2015).

The FF expression of some miRNAs was also modulated by the gonadotropin treatment. MiR-29a was significantly down-regulated and miR-140 overexpressed in FF pools from women who were stimulated with hMG compared with those treated with r-FSH. This is in agreement with a previous study showing that miR-29a is significantly down-regulated by FSH treatment in cultured rat granulosa cells, thus influencing progesterone production (Yao et al., 2010). Our data suggest that gonadotropin treatments could affect intra-follicular miRNA expression and ultimately IVF efficacy. We also found that total high dose of gonadotropins was associated with miR-140 up-regulation. This probably reflects a potential dose-effect relationship of gonadotropins on FF miR-140 expression profile. Further studies are required to investigate the biological mechanisms involved in gonadotropin effect on the intra-follicular expression of these miRNAs.

The importance of miRNAs in early embryo development has been demonstrated in many mammalian species (Suh and Blelloch, 2011). Although Feng et al., did not observe significant differential expression of let-7b in FF samples according to embryo quality (Feng et al., 2015), we found that FF let-7b level was significantly related to the embryo developmental potential. Indeed, let-7b levels in FF predicted significantly blastocyst formation and expansion in women with normal ovarian reserve. It was previously shown that let-7 can regulate developmental timing in *Caenorhabditis elegans* (Reinhart et al., 2000). However, let-7b role in blastocyst formation remains unclear. FF let-7b might represent a new predictive biomarker of blastocyst development that could be useful to define the best strategy of embryo culture during IVF.

In addition, FF miR-29a levels predicted significantly the clinical pregnancy outcome with higher sensitivity (83.3%) compared to the top quality embryos proportion in our cohort. MiR-29a is highly expressed in rat uterus during embryo implantation and its expression is regulated by blastocyst activation and uterine decidualization (Xia et al., 2014). Interestingly, miR-29a expression might influence pregnancy outcome by acting both on the follicular and endometrial side, supporting the hypothesis that favorable follicular and endometrial environments are necessary for conception.

In conclusion, our study shows that, during IVF, miRNA expression profiling in human FF samples provide biomarkers to efficiently and easily identify ovarian reserve disorders and to predict blastocyst development and clinical pregnancy outcomes. These new potential biomarkers could be used in the daily practice to improve personalized IVF strategies and to identify new therapeutic targets in female infertility management.

TABLE 5

Multivariate logistic model showing the association of specific FF mRNAs with polycystic ovary syndrome (PCOS) and low function ovarian reserve (LFOR). OR, Odds ratio, FF, follicular fluid.

| | Univariate analysis | | Multivariate analysis | |
|---|---|---|---|---|

Relative FF microRNAs expression related to PCOS

| FF microRNAs | Cudde OR [95% CI] | p-value | Adjusted OR [95% CI] | p-value |
|---|---|---|---|---|
| FF miR-30a | 4.5 [1.94; 10.57] | p < 0.001 | 5.0 [1.86; 13.68] | 0.001 |
| FF miR-140 | 0.6 [0.37; 0.96] | 0.03 | 0.52 [0.29; 0.94] | 0.03 |
| FF let-7b | 1.0 [0.99; 1.0] | 0.01 | 1.0 [0.99; 1.0] | 0.02 |

Relative FF microRNAs expression related to LFOR

| FF microRNAs | Cudde OR [95% CI] | p-value | Adjusted OR [95% CI] | p-value |
|---|---|---|---|---|
| FF miR-30a | 4.0 [0.87; 18.23] | 0.07 | 2.8 [0.56; 13.92] | 0.21 |
| FF miR-191 | 1.4 [1.03; 1.93] | 0.03 | 1.4 [0.98; 1.87] | 0.07 |

TABLE 6

Power of discrimination of FF miRNA expressions for PCOS and LFOR identification. MiRNAs were analyzed individually and in combination.

| | Prediction for PCOS | | | | Prediction for LFOR | | |
|---|---|---|---|---|---|---|---|
| ROC analysis | FF miR-30a | FF miR-140 | FF let-7b | Combination of FF miR-30a, miR-140 and let-7b | FF miR-30a | FF miR-191 | Combination of FF miR-30a and miR-191 |
| AuROC (95% CI) | 0.67 (0.57-0.76) | 0.67 (0.57-0.76) | 0.67 (0.57-0.76) | 0.83 (0.73-0.92) | 0.79 (0.68-0.87) | 0.77 (0.67-0.86) | 0.84 (0.67-0.86) |
| p-value | 0.02 | 0.007 | 0.003 | <0.0001 | <0.0001 | 0.002 | <0.0001 |
| Sensitivity (%) | 57.7 | 57.7 | 53.9 | 70.0 | 100 | 57.1 | 85.9 |
| Specificity (%) | 85.1 | 81.1 | 75.7 | 83.8 | 53.9 | 92.3 | 71.4 |
| Positive predictive value (%) | 57.7 | 51.7 | 41.9 | 60 | 16.3 | 40 | 31.3 |
| Negative predictive value (%) | 85.1 | 84.5 | 81.2 | 88.6 | 100 | 96 | 97.1 |
| Cut-off value | >0.49 | ≤0.92 | ≤93.95 | — | >0.14 | >2.98 | — |

TABLE 7

Clinical characteristics of all patients (n = 131) and of each groups: women with normal ovarian reserve (n = 91), with PCOS (n = 30), or LFOR (n = 10).

| Variable | Total (n = 131) | | Normal ovarian reserve (n = 91) | | PCOS (n = 30) | | LFOR (n = 10) | |
|---|---|---|---|---|---|---|---|---|
| | Mean ± SD | n (%) | Mean = SD | n (%) | Mean ± SD | n (%) | Mean ± SD | n (%) |
| Age (years) | 34.7 ± 1.5 | — | 34.3 ± 5.1 | — | 33.1 ± 3.8 | — | 36.8 ± 4.6 | — |
| BMI (kg/m$^2$) | 23.4 ± 4.5 | — | 22.8 ± 3.7 | — | 25.4 ± 5.3 | — | 22.1 ± 4.6 | — |
| 18.5 ≤ BMI < 25 | — | 83 (63.4) | — | 66 (72.5) | — | 11 (36.7) | — | 7 (70.0) |
| BMI<18.5 | — | 9 (6.9) | — | 4 (4.4) | — | 3 (10.0) | — | 1 (10.0) |
| 25 ≤ BMI < 30 | — | 29 (22.1) | — | 17 (18.7) | — | 11 (36.7) | — | 1 (10.0) |

TABLE 7-continued

Clinical characteristics of all patients (n = 131) and of each groups: women with normal ovarian reserve (n = 91), with PCOS (n = 30), or LFOR (n = 10).

| Variable | Total (n = 131) Mean ± SD | n (%) | Normal ovarian reserve (n = 91) Mean ± SD | n (%) | PCOS (n = 30) Mean ± SD | n (%) | LFOR (n = 10) Mean ± SD | n (%) |
|---|---|---|---|---|---|---|---|---|
| BMI ≥30 | — | 10 (7.6) | — | 4 (4.4) | — | 5 (16.6) | — | 1 (10.0) |
| Infertility lenght (years) | 3.6 ± 1.5 | — | 3.3 ± 1.6 | — | 3.9 ± 1.6 | — | 3.8 ± 1.4 | — |
| Infertility aetiology | | | | | | | | |
| Male facts | — | 41 (31.3) | — | 37 (40.6) | — | 2 (6.6) | — | 2 (20.0) |
| Female factor | — | 49 (37.4) | — | 38 (41.8) | — | 8 (26.7) | — | 5 (50.0) |
| Mixed infertility | — | 33 (25.2) | — | 8 (8.8) | — | 20 (66.7) | — | 3 (30.0) |
| Unexplained infertility | — | 8 (6.1) | — | 8 (8.8) | — | 0 (0) | — | 0 (0) |
| Primary infertility | — | 78 (59.5) | — | 57 (62.6) | — | 14 (46.7) | — | 7 (70.0) |
| Secondary infertility | — | 53 (40.5) | — | 34 (37.4) | — | 16 (53.3) | — | 3 (30.0) |
| IVF/ICSI cycle number | 2.1 ± 1.3 | — | 2.2 ± 1.3 | — | 1.9 ± 1.1 | — | 2.2 ± 1.4 | — |
| 1 | — | 51 (38.9) | — | 34 (37.4) | — | 12 (40.0) | — | 5 (50.0) |
| >1 | — | 80 (61.1) | — | 56 (42.7) | — | 18 (60.0) | — | 5 (50.0) |
| Baseline evaluation | | | | | | | | |
| FSH (IU/l) | 8.3 ± 1.8 | — | 7.2 ± 2.3 | — | 6.1 ± 1.7 | — | 11.6 ± 3.1 | — |
| LH (IU/l) | 7.1 ± 3.7 | — | 5.6 ± 2.1 | — | 8.2 ± 4.5 | — | 7.4 ± 4.5 | — |
| E2 (pg/ml) | 47.7 ± 35.2 | — | 45.9 ± 39.2 | — | 41.9 ± 15.4 | — | 55.3 ± 20.9 | — |
| AMH (ng/ml) | 4.1 ± .24 | — | 3.1 ± 1.7 | — | 8.0 ± 5.4 | — | 1.1 ± 0.5 | — |
| AFC | 16 ± 6 | — | 16 ± 6 | — | 27 ± 11 | — | 6 ± 2 | — |
| Agonist protocol* | — | 63 (48.1) | — | 39 (42.9) | — | 19 (63.3) | — | 5 (50.0) |
| Antagonist protocol | — | 64 (48.9) | — | 48 (52.7) | — | 11 (63.7) | — | 5 (50.0) |
| Days of stimulation | 10.5 ± 1.4 | — | 10 ± 1.3 | — | 10.4 ± 1.7 | — | 11.1 ± 1.3 | — |
| Total dose of gonadotropins (IU/l) | 2501 ± 673 | — | 2321.7 ± 912.5 | — | 1851.4 ± 706.3 | — | 3330 ± 400.1 | — |
| r-FSH | — | 73 (55.8) | — | 45 (49.4) | — | 24 (80.0) | — | 4 (40.0) |
| HP-hMG | — | 54 (41.2) | — | 42 (46.2) | — | 6 (20.0) | — | 6 (60.0) |
| Hormonal ovarian response at ovulation triggering | | | | | | | | |
| Peak E2 level (pg/ml) | 1552 ± 668.2 | — | 1764.5 ± 728.3 | — | 1656.9 ± 737.6 | — | 1234.7 ± 538.7 | — |
| Progesterone level (ng/ml) | 0.8 ± 0.4 | — | 0.9 ± 0.4 | — | 0.8 ± 0.4 | — | 0.7 ± 0.4 | — |
| LH level (IU/l) | 2.1 ± 1.7 | — | 2.0 ± 1.4 | — | 2.4 ± 2.1 | — | 2.0 ± 1.6 | — |
| FIV | — | 32 (24.4) | — | 23 (25.3) | — | 5 (16.7) | — | 4 (40.0) |
| ICSI | — | 99 (75.6) | — | 68 (74.7) | — | 25 (83.3) | — | 6 (60.0) |

SD, standard deviation;
BMI, body mass index;
E2, 17β-estradiol;
AMH, anti-Mullerian hormone;
AFC, antral follicle count;
r-FSH, recombinant follicle-stimulating hormone;
HP-hMG, highly purified human menopausal gonadotropin
*Except four women who received mild stimulation.

TABLE 8

IVF outcomes of all patients (n = 131) and of each groups: women with normal ovarian reserve (n = 91), with PCOS (n = 30), or LFOR (n = 10).

| IVF outcomes | Total (n = 31) Mean | SD | n | Normal ovarian reserve (n = 91) Mean | SD | n | PCOS (n = 30) Mean | SD | n | LFOR (n = 10) Mean | SD | n |
|---|---|---|---|---|---|---|---|---|---|---|---|---|
| Retrieved oocytes | 7.6 | 4.5 | — | 9.0 | 4.2 | — | 9.1 | 4.8 | — | 4.7 | 4.5 | — |
| Mature oocytes (MII) | 6.0 | 3.7 | — | 7.8 | 4.1 | — | 6.4 | 3.6 | — | 3.7 | 3.4 | — |
| ≤2 | — | — | 14 | — | — | 9 | — | — | 1 | — | — | 4 |
| >2 | — | — | 85 | — | — | 59 | — | — | 24 | — | — | 2 |
| Maturity rate (%) | 77 | — | — | 81 | — | — | 71 | — | — | 80 | — | — |
| IVF/ICSI fertilization rate (%) | 64 | — | — | 67 | — | — | 60 | — | — | 65 | — | — |
| At 25-27 hours after fertilization | | | | | | | | | | | | |
| Early cleavage | 1.3 | 1.4 | — | 2.2 | 2.1 | — | 1.2 | 1.6 | — | 0.5 | 0.5 | — |
| At Day 2 | | | | | | | | | | | | |
| Embryo | 4.1 | 3.3 | — | 4.8 | 3.7 | — | 4.6 | 3.3 | — | 2.8 | 3.0 | — |
| At Day 3 | | | | | | | | | | | | |
| Top quality embryo | 1.2 | 1.6 | — | 1.6 | 1.8 | — | 1.2 | 1.7 | — | 0.8 | 1.3 | — |

TABLE 8-continued

IVF outcomes of all patients (n = 131) and of each groups: women with normal ovarian reserve (n = 91), with PCOS (n = 30), or LFOR (n = 10).

| IVF outcomes | Total (n = 31) | | | Normal ovarian reserve (n = 91) | | | PCOS (n = 30) | | | LFOR (n = 10) | | |
|---|---|---|---|---|---|---|---|---|---|---|---|---|
| | Mean | SD | n | Mean | SD | n | Mean | SD | n | Mean | SD | n |
| Total fragmentation rate (%) At Day 5 | 15 | — | — | 14 | — | — | 17 | — | — | 15 | — | — |
| Blastulation rate (Blastocyst/prolonged culture embryos) (%) | 31 | — | — | 46 | — | — | 38 | — | — | 8 | — | — |
| Expanded blastocyst rate (Expanded blastocyst/blastocysts) (%) | 45 | — | — | 52 | — | — | 38 | — | — | — | — | — |
| Clinical pregancy rate per transfer (%) | 27 | — | — | 38 | — | — | 29 | — | — | 14 | — | — |
| Singleton pregnancy | — | — | 31 | — | — | 22 | — | — | 9 | — | — | 1 |
| Multiple pregnancy | — | — | 2 | — | — | 1 | — | — | 1 | — | — | 0 |

SD, standard deviation;
MII, oocyte blocked in meiotic metaphase II.

TABLE 9

Circulating miRNAs expressed in the cumulus-oocyte complex (COC), granulosa cells (GC), cumulus cells (CC) and in follicular fluid (FF): their functions and primary targets in ovarian follicles.

| miRNAs | Expression | Species | Regulation | Target genes | Functions | References |
|---|---|---|---|---|---|---|
| let-7b | CC | Human | — | | Regulation of COC | Assou et al. (2013) |
| | GC | Porcine | — | — | Ovary follicle atresia | Cao et al. (2015) |
| | GC | Mouse | — | | Follicular development | Yao et al. (2009) |
| | Ovary | Goat | — | Activin receptor 1, Smad 2/3 | Follicular development | Zhang et al. (2013) |
| | COC | Bovine | — | — | Oogenesis | Miles et al. (2012) |
| miR-29a | CC | Human | — | DNMT 3A/3B | Meiosis resumption | Santonocito et al. (2014) |
| | GC (culture) | Rat | Regulation by FSH | COL4A1 and BMF | Progesterone production | Yao et al. (2010) |
| miR-30a | GC COV43 (culture) | Human | | FOXL2, BCL2A1, IER3 and cyclin D2 | Cell proliferation | Wang et al. (2015) |
| miR-320a | FF | Human | — | — | Embryo quality | Feng et al. (2015) |
| | FF | Human | — | — | PCOS | Sang et al. (2013) |
| | GC | Mouse | Regulation by FSH and by miR-383 | E2F1 and SF-1 | Cell proliferation, oestrogen secretion | Yin et al. (2014) |
| | Oocytes/embryos | Mouse | — | Wnt signaling pathway genes | Oocyte quality/Embryo developement | Feng et al. (2015) |

Example 4

Circulating Nucleic Acids in Serum Samples as Biomarkers of Ovarian Reserve, Ovarian Function and Disorders.

CfDNA Quantification at Day 3 of Menstrual Cycle in Serum Samples from 92 Women. Mean±SD=0.25±0.14

The inventors demonstrated that cfDNA level in serum was significantly higher in women with LFOR compared to women with normal ovarian reserve (p=0.045) (FIG. 12A). cfDNA level in serum tended to be higher in women with PCOS compared to women with normal ovarian reserve (p=0.05) (FIG. 12A)

At day 3 of menstrual cycle, cfDNA level in serum predicted significantly LFOR (AUC=0.64; Se=52%; SP=75%; cutoff>0.17). At day 3 of menstrual cycle, cfDNA level in serum predicted significantly PCOS (AUC=0.65; Se=95%; SP=34%; cutoff>0.06) (FIG. 12B).

cfDNA level in serum was significantly higher in older women (age>36 ou age≥36 years) compared to young women (age<36 or age≤36 years) (p=0.037; p=0.024, respectively) as shown in FIG. 12C. cfDNA level in serum at day 3 of menstrual cycle was significantly and positively correlated with women's age (r=0.27; p=0.02) (FIG. 12D).

For women undergoing IVF/ICSI procedure (n=26), at day 3 of menstrual cycle, cfDNA level was significantly higher in serum samples from women who obtained less than 6 oocytes at oocyte day (≤6 oocytes) compared to those who obatained more than 6 oocytes (>6 oocytes) (p=0.013) (FIG. 12E). cfDNA level at day 3 of menstrual cycle could predict the number of retrieved oocyte and thus IVF/ICSI prognosis (FIG. 12F).

The inventors also performed for patients with normal ovarian reserve and with LFOR (PCOS were excluded from this analysis) a comparison of cfDNA with AMH level at day 3 of menstrual cycle, the classical biomarker used to assess ovarian reserve. At day 3 of menstrual cycle, cfDNA level was significantly higher in serum samples from women with AMH≤1 ng/ml or ≤2 ng/ml compared to those with AMH>1 ng/ml or >2 ng/ml, respectively (p=0.046; p=0.004, respectively) (FIG. 12G). cfDNA level in serum at day 3 of menstrual cycle was significantly and negatively correlated with AMH level in serum at day 3 of menstrual cycle (r=−0.32; p=0.006) (FIG. 12H).

All patients were also included in this analysis (n=92). At day 3 of menstrual cycle, cfDNA level was significantly higher in serum samples from women with AMH≤2 ng/ml compared to those with AMH between 2 and 5 ng/ml (p=0.013). At day 3 of menstrual cycle, cfDNA level tended to be higher in serum samples from women with AMH≥5 ng/ml compared to those with AMH between 2 and 5 ng/ml (p=0.09) (FIG. 12I).

MicroRNAs Expression at Day 3 of Menstrual Cycle in Serum Samples from 70 Women.

The inventors demonstrated that let-7b expression in serum was higher in older women (age≥38 years) compared to women aged less than 38 years old (FIG. 13A).

miR-30d, and miR-320a expression decreased significantly in women with high LH levels (>5 IU/l) compared to women normal LH levels (between 3-5 IU/l) (p<0.03; p<0.02; p<0.02, respectively) (FIG. 13B).

REFERENCES

Throughout this application, various references describe the state of the art to which this invention pertains. The disclosures of these references are hereby incorporated by reference into the present disclosure.

Albertini D F, Combelles C M, Benecchi E and Carabatsos M J. Cellular basis for paracrine regulation of ovarian follicle development. Reproduction 2001; 121:647-653.

Assou S, Haouzi D, Dechaud H, Gala A, Ferrieres A and Hamamah S. Comparative gene expression profiling in human cumulus cells according to ovarian gonadotropin treatments. Biomed Res Int 2013; 2013:354582.

Azhar S. MicroRNA-122: A New Player in the Negative Regulation of LH Receptor Expression by the LH Receptor mRNA Binding Protein (LRBP). Endocrinology 2013; 154:4439-4442.

Bauer M, Hutterer G, Eder M, Majer S, Leshane E, Johnson K L, Peter I, Bianchi D W and Pertl B. A prospective analysis of cell-free fetal DNA concentration in maternal plasma as an indicator for adverse pregnancy outcome. Prenat Diagn 2006; 26:831-836.

Bischoff F Z, Lewis D E and Simpson J L. Cell-free fetal DNA in maternal blood: kinetics, source and structure. Hum Reprod Update 2005; 11:59-67.

Bischoff F Z, Sinacori M K, Dang D D, Marquez-Do D, Horne C, Lewis D E and Simpson J L. Cell-free fetal DNA and intact fetal cells in maternal blood circulation: implications for first and second trimester non-invasive prenatal diagnosis. Hum Reprod Update 2002; 8:493-500.

Broer S L, van Disseldorp J, Broeze K A, Dolleman M, Opmeer B C, Bossuyt P, Eijkemans M J, Mol B W and Broekmans F J. Added value of ovarian reserve testing on patient characteristics in the prediction of ovarian response and ongoing pregnancy: an individual patient data approach. Hum Reprod Update 2013; 19:26-36.

Caburet S, Georges A, L'Hote D, Todeschini A L, Benayoun B A and Veitia R A. The transcription factor FOXL2: at the crossroads of ovarian physiology and pathology. Mol Cell Endocrinol 2012; 356:55-64.

Carletti M Z and Christenson L K. MicroRNA in the ovary and female reproductive tract. J Anim Sci 2009; 87:E29-38.

Carletti M Z, Fiedler S D and Christenson L K. MicroRNA 21 blocks apoptosis in mouse periovulatory granulosa cells. Biol Reprod 2010; 83:286-295.

Chaffin C L, Schwinof K M and Stouffer R L. Gonadotropin and steroid control of granulosa cell proliferation during the periovulatory interval in rhesus monkeys. Biol Reprod 2001; 65:755-762.

Cho W C. OncomiRs: the discovery and progress of microRNAs in cancers. Mol Cancer 2007; 6:60.

Chou J S, Jacobson J D, Patton W C, King A and Chan P J. Modified isocratic capillary electrophoresis detection of cell-free DNA in semen. J Assist Reprod Genet 2004; 21:397-400.

Conn P M and Crowley W F, Jr. Gonadotropin-releasing hormone and its analogs. Annu Rev Med 1994; 45:391-405.

Czamanski-Cohen J, Sarid O, Cwikel J, Lunenfeld E, Douvdevani A, Levitas E and Har-Vardi I. Increased plasma cell-free DNA is associated with low pregnancy rates among women undergoing IVF-embryo transfer. Reprod Biomed Online 2013; 26:36-41.

Dai A, Sun H, Fang T, Zhang Q, Wu S, Jiang Y, Ding L, Yan G and Hu Y. MicroRNA-133b stimulates ovarian estradiol synthesis by targeting Fox12. FEBS Lett 2013; 587:2474-2482.

Dillhoff M, Liu J, Frankel W, Croce C and Bloomston M. MicroRNA-21 is overexpressed in pancreatic cancer and a potential predictor of survival. J Gastrointest Surg 2008; 12:2171-2176.

Fiedler S D, Carletti M Z, Hong X and Christenson L K. Hormonal regulation of MicroRNA expression in periovulatory mouse mural granulosa cells. Biol Reprod 2008; 79:1030-1037.

Gilchrist R B, Lane M and Thompson J G. Oocyte-secreted factors: regulators of cumulus cell function and oocyte quality. Hum Reprod Update 2008; 14:159-177.

Godoy J, Nishimura M and Webster N J. Gonadotropin-releasing hormone induces miR-132 and miR-212 to regulate cellular morphology and migration in immortalized LbetaT2 pituitary gonadotrope cells. Mol Endocrinol 2011; 25:810-820.

Hasuwa H, Ueda J, Ikawa M and Okabe M. miR-200b and miR-429 function in mouse ovulation and are essential for female fertility. Science 2013; 341:71-73.

Hawkins S M and Matzuk M M. Oocyte-somatic cell communication and microRNA function in the ovary. Ann Endocrinol (Paris) 2010; 71:144-148.

Hossain M M, Sohel M M, Schellander K and Tesfaye D. Characterization and importance of microRNAs in mammalian gonadal functions. Cell Tissue Res 2012; 349:679-690.

Kaiser U B, Conn P M and Chin W W. Studies of gonadotropin-releasing hormone (GnRH) action using GnRH receptor-expressing pituitary cell lines. Endocr Rev 1997; 18:46-70.

Kim Y J, Ku S Y, Kim Y Y, Liu H C, Chi S W, Kim S H, Choi Y M, Kim J G and Moon S Y. MicroRNAs transfected into granulosa cells may regulate oocyte meiotic competence during in vitro maturation of mouse follicles. Hum Reprod 2013; 28:3050-3061.

Lagos-Quintana M, Rauhut R, Lendeckel W and Tuschl T. Identification of novel genes coding for small expressed RNAs. Science 2001; 294:853-858.

Lambert-Messerlian G, Kloza E M, Williams J, 3rd, Loucky J, O'Brien B, Wilkins-Haug L, Mahoney M J, De Biasio P, Borrell A, Ehrich M et al. Maternal plasma DNA testing for aneuploidy in pregnancies achieved by assisted reproductive technologies. Genet Med 2013.

Lee R C, Feinbaum R L and Ambros V. The C. elegans heterochronic gene lin-4 encodes small RNAs with antisense complementarity to lin-14. Cell 1993; 75:843-854.

Lo Y M and Chiu R W. Noninvasive prenatal diagnosis of fetal chromosomal aneuploidies by maternal plasma nucleic acid analysis. Clin Chem 2008; 54:461-466.

Lo Y M, Lau T K, Zhang J, Leung T N, Chang A M, Hjelm N M, Elmes R S and Bianchi D W. Increased fetal DNA concentrations in the plasma of pregnant women carrying fetuses with trisomy 21. Clin Chem 1999; 45:1747-1751.

Menon B, Sinden J, Franzo-Romain M, Botta R B and Menon K M. Regulation of LH Receptor mRNA Binding Protein by miR-122 in Rat Ovaries. Endocrinology 2013; 154:4826-4834.

Miles J R, McDaneld T G, Wiedmann R T, Cushman R A, Echtemkamp S E, Vallet J L and Smith T P.

Mitchell P S, Parkin R K, Kroh E M, Fritz B R, Wyman S K, Pogosova-Agadjanyan E L, Peterson A, Noteboom J, O'Briant K C, Allen A et al. Circulating microRNAs as stable blood-based markers for cancer detection. Proc Natl Acad Sci USA 2008; 105:10513-10518.

Nagaraja A K, Andreu-Vieyra C, Franco H L, Ma L, Chen R, Han D Y, Zhu H, Agno J E, Gunaratne P H, DeMayo F J et al. Deletion of Dicer in somatic cells of the female reproductive tract causes sterility. Mol Endocrinol 2008; 22:2336-2352.

Pangas S A, Choi Y, Ballow D J, Zhao Y, Westphal H, Matzuk M M and Rajkovic A. Oogenesis requires germ cell-specific transcriptional regulators Sohlh1 and Lhx8. Proc Natl Acad Sci USA 2006; 103:8090-8095.

Pisarska M D, Barlow G and Kuo F T. Minireview: roles of the forkhead transcription factor FOXL2 in granulosa cell biology and pathology. Endocrinology 2011; 152:1199-1208.

Robker R L and Richards J S. Hormone-induced proliferation and differentiation of granulosa cells: a coordinated balance of the cell cycle regulators cyclin D2 and p27Kip1. Mol Endocrinol 1998; 12:924-940.

Sang Q, Yao Z, Wang H, Feng R, Zhao X, Xing Q, Jin L, He L, Wu L and Wang L. Identification of microRNAs in human follicular fluid: characterization of microRNAs that govern steroidogenesis in vitro and are associated with polycystic ovary syndrome in vivo. J Clin Endocrinol Metab 2013; 98:3068-3079.

Schmidt D, Ovitt C E, Anlag K, Fehsenfeld S, Gredsted L, Treier A C and Treier M. The murine winged-helix transcription factor Fox12 is required for granulosa cell differentiation and ovary maintenance. Development 2004; 131:933-942.

Schwarzenbach H, Milde-Langosch K, Steinbach B, Muller V and Pantel K. Diagnostic potential of PTEN-targeting miR-214 in the blood of breast cancer patients. Breast Cancer Res Treat 2012; 134:933-941.

Thomas M, Lieberman J and Lal A. Desperately seeking microRNA targets. Nat Struct Mol Biol 2010; 17:1169-1174.

Umetani N, Kim J, Hiramatsu S, Reber H A, Hines O J, Bilchik A J and Hoon D S. Increased integrity of free circulating DNA in sera of patients with colorectal or periampullary cancer: direct quantitative PCR for ALU repeats. Clin Chem 2006; 52:1062-1069.

Valadi H, Ekstrom K, Bossios A, Sjostrand M, Lee J J and Lotvall J O. Exosome-mediated transfer of mRNAs and microRNAs is a novel mechanism of genetic exchange between cells. Nat Cell Biol 2007; 9:654-659.

Verghese E T, Hanby A M, Speirs V and Hughes T A. Small is beautiful: microRNAs and breast cancer-where are we now? J Pathol 2008; 215:214-221.

Visser J A, de Jong F H, Laven J S and Themmen A P. Anti-Mullerian hormone: a new marker for ovarian function. Reproduction 2006; 131:1-9.

Weenen C, Laven J S, Von Bergh A R, Cranfield M, Groome N P, Visser J A, Kramer P, Fauser B C and Themmen A P. Anti-Mullerian hormone expression pattern in the human ovary: potential implications for initial and cyclic follicle recruitment. Mol Hum Reprod 2004; 10:77-83.

Wright C F and Burton H. The use of cell-free fetal nucleic acids in maternal blood for non-invasive prenatal diagnosis. Hum Reprod Update 2009; 15:139-151.

Wu C, Ding X, Li H, Zhu C and Xiong C. Genome-wide promoter methylation profile of human testis and epididymis: identified from cell-free seminal DNA. BMC Genomics 2013; 14:288.

Yao N, Lu C L, Zhao J J, Xia H F, Sun D G, Shi X Q, Wang C, Li D. Cui Y and Ma X. A network of miRNAs expressed in the ovary are regulated by FSH. Front Biosci (Landmark Ed) 2009; 14:3239-3245.

Yao N, Yang B Q, Liu Y, Tan X Y, Lu C L, Yuan X H and Ma X. Follicle-stimulating hormone regulation of microRNA expression on progesterone production in cultured rat granulosa cells. Endocrine 2010; 38:158-166.

The invention claimed is:

1. A method for treating a woman with a controlled ovarian hyperstimulation (COS), comprising the steps of:
   i) providing from a woman who has received a COS treatment, a follicular fluid sample;
   ii) extracting miR-140 from the follicular fluid sample;
   iii) quantifying the level of miR-140 in the sample;
   iv) identifying the woman as being responsive to COS treatment when the level of miR-140 is increased in comparison to the level of miR-140 in control follicular fluid samples obtained from women with normal ovarian reserve, and
   v) continuing to administer the COS treatment to the woman identified as being responsive to COS treatment.

* * * * *